(12) United States Patent
Dees, Jr. et al.

(10) Patent No.: US 9,089,343 B2
(45) Date of Patent: Jul. 28, 2015

(54) LOCKING INSTRUMENT ASSEMBLY

(75) Inventors: Roger Ryan Dees, Jr., Senatobia, MS (US); Jeffrey N. Yeager, Nesbit, MS (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/618,542

(22) Filed: Sep. 14, 2012

(65) Prior Publication Data
US 2013/0012941 A1 Jan. 10, 2013

Related U.S. Application Data

(63) Continuation of application No. 12/089,177, filed as application No. PCT/US2006/038859 on Oct. 3, 2006, now Pat. No. 8,277,450.

(60) Provisional application No. 60/723,228, filed on Oct. 3, 2005, provisional application No. 60/725,345, filed on Oct. 11, 2005.

(51) Int. Cl.
*A61F 5/00* (2006.01)
*A61B 17/15* (2006.01)
*A61B 17/17* (2006.01)
*A61B 17/00* (2006.01)

(52) U.S. Cl.
CPC ........... *A61B 17/154* (2013.01); *A61B 17/1717* (2013.01); *A61B 17/1764* (2013.01); *A61B 2017/00477* (2013.01); *Y10T 279/17299* (2015.01); *Y10T 279/17504* (2015.01); *Y10T 279/17538* (2015.01)

(58) Field of Classification Search
CPC .......................... A61B 17/7233; A61B 17/1764
USPC ............................... 606/62, 67, 86 R, 87, 96
See application file for complete search history.

(56) References Cited

U.S. PATENT DOCUMENTS

| | | | |
|---|---|---|---|
| 2,309,502 A | | 1/1943 | Douglas |
| 3,918,727 A | * | 11/1975 | Forsythe ........................ 279/50 |
| 3,949,643 A | * | 4/1976 | Mucci et al. .................. 409/288 |
| 4,393,868 A | | 7/1983 | Teague |
| 4,471,993 A | | 9/1984 | Watson |
| RE31,809 E | | 1/1985 | Danieletto et al. |
| 4,604,997 A | | 8/1986 | De Bastiani et al. |

(Continued)

FOREIGN PATENT DOCUMENTS

| | | |
|---|---|---|
| DE | 198528770 U1 | 1/1986 |
| WO | WO9730640 A1 | 8/1997 |
| WO | WO9925263 A1 | 5/1999 |

OTHER PUBLICATIONS

International Search Report for International Application No. PCT/US2006/038859, mailed Feb. 2, 2007,3 pages.

(Continued)

*Primary Examiner* — Eduardo C Robert
*Assistant Examiner* — Stuart S Bray
(74) *Attorney, Agent, or Firm* — Fish & Richardson P.C.

(57) ABSTRACT

A locking instrument assembly for use in conjunction with an intramedullary device is disclosed. The locking instrument assembly includes an inner collet, an outer body, and a knob. The inner collet has a collar and a fastener member. The knob engages the fastener member to press the outer body against the collar. As the knob mates with the fastener member, the collar applies a clamping force to the intramedullary device.

45 Claims, 30 Drawing Sheets

(56) References Cited

U.S. PATENT DOCUMENTS

| | | | |
|---|---|---|---|
| 4,736,742 A | 4/1988 | Alexson et al. | |
| 4,834,092 A | 5/1989 | Alexson et al. | |
| 4,887,865 A | 12/1989 | Dawidzon | |
| 4,936,843 A | 6/1990 | Sohngen | |
| 4,952,213 A * | 8/1990 | Bowman et al. | 606/79 |
| 4,976,713 A | 12/1990 | Landanger et al. | |
| 5,003,965 A | 4/1991 | Talish et al. | |
| 5,035,700 A | 7/1991 | Kenna | |
| 5,049,151 A | 9/1991 | Durham et al. | |
| 5,053,037 A * | 10/1991 | Lackey | 606/79 |
| 5,100,408 A * | 3/1992 | Lackey | 606/79 |
| 5,228,459 A * | 7/1993 | Caspari et al. | 128/898 |
| 5,282,803 A * | 2/1994 | Lackey | 606/80 |
| 5,304,181 A * | 4/1994 | Caspari et al. | 606/80 |
| 5,305,203 A | 4/1994 | Raab | |
| 5,330,501 A * | 7/1994 | Tovey et al. | 606/198 |
| 5,360,431 A | 11/1994 | Puno et al. | |
| 5,368,549 A | 11/1994 | McVicker | |
| 5,454,810 A | 10/1995 | Pohl et al. | |
| 5,456,655 A | 10/1995 | Morris | |
| 5,462,550 A | 10/1995 | Dielz et al. | |
| 5,484,446 A | 1/1996 | Burke et al. | |
| 5,514,140 A * | 5/1996 | Lackey | 606/80 |
| 5,549,703 A | 8/1996 | Daigle et al. | |
| 5,556,374 A | 9/1996 | Grace et al. | |
| 5,658,292 A * | 8/1997 | Axelson, Jr. | 606/86 R |
| 5,667,507 A | 9/1997 | Corin et al. | |
| 5,674,225 A * | 10/1997 | Muller | 606/99 |
| 5,683,397 A | 11/1997 | Vendrely et al. | |
| 5,697,158 A | 12/1997 | Klinzing et al. | |
| 5,700,268 A | 12/1997 | Bertiin | |
| 5,711,297 A | 1/1998 | Iliff | |
| 5,725,532 A | 3/1998 | Shoemaker | |
| 5,748,767 A | 5/1998 | Raab | |
| 5,810,829 A * | 9/1998 | Elliott et al. | 606/80 |
| 5,827,208 A | 10/1998 | Mason et al. | |
| 5,891,150 A * | 4/1999 | Chan | 606/96 |
| 5,908,424 A * | 6/1999 | Bertin et al. | 606/88 |
| 5,910,143 A * | 6/1999 | Cripe et al. | 606/87 |
| 5,928,234 A | 7/1999 | Manspeizer | |
| 5,980,475 A | 11/1999 | Gibbons | |
| 6,027,507 A | 2/2000 | Anderson et al. | |
| 6,077,270 A | 6/2000 | Katz | |
| 6,139,548 A | 10/2000 | Errico | |
| 6,162,228 A | 12/2000 | Durham | |
| 6,162,234 A | 12/2000 | Freedland et al. | |
| 6,168,595 B1 * | 1/2001 | Durham et al. | 606/64 |
| 6,175,979 B1 | 1/2001 | Jackson | |
| 6,193,724 B1 | 2/2001 | Chan | |
| RE37,338 E | 8/2001 | McVicker | |
| 6,290,704 B1 | 9/2001 | Burkinshaw et al. | |
| 6,300,941 B1 | 10/2001 | Segalle | |
| 6,344,043 B1 * | 2/2002 | Pappas | 606/96 |
| 6,402,756 B1 | 6/2002 | Ralph et al. | |
| 6,436,058 B1 | 8/2002 | Krahner et al. | |
| 6,447,548 B1 | 9/2002 | Ralph et al. | |
| 6,532,002 B2 | 3/2003 | Segalle | |
| 6,554,864 B2 | 4/2003 | Ralph et al. | |
| 6,558,423 B1 | 5/2003 | Michelson | |
| 6,575,980 B1 | 6/2003 | Robie et al. | |
| 6,595,936 B1 | 7/2003 | Oladipo | |
| 6,595,994 B2 | 7/2003 | Kilpela et al. | |
| 6,605,092 B2 | 8/2003 | Grumberg et al. | |
| 6,666,867 B2 | 12/2003 | Ralph et al. | |
| 6,673,114 B2 | 1/2004 | Hartdegen et al. | |
| 6,689,134 B2 | 2/2004 | Ralph et al. | |
| 6,712,823 B2 * | 3/2004 | Grusin et al. | 606/87 |
| 6,729,794 B2 | 5/2004 | Callaway et al. | |
| 6,746,453 B2 | 6/2004 | Deloge et al. | |
| 6,837,904 B2 | 1/2005 | Ralph et al. | |
| 6,890,356 B2 | 5/2005 | Ralph et al. | |
| 6,916,325 B2 | 7/2005 | Kana et al. | |
| 6,925,339 B2 | 8/2005 | Grimm et al. | |
| 6,951,561 B2 | 10/2005 | Warren et al. | |
| 6,974,483 B2 | 12/2005 | Murray | |
| 6,991,802 B1 | 1/2006 | Ahola et al. | |
| 7,001,346 B2 | 2/2006 | White | |
| 7,008,422 B2 | 3/2006 | Foley et al. | |
| 7,041,135 B2 | 5/2006 | Michelson | |
| 7,601,155 B2 | 10/2009 | Petersen | |
| 7,618,420 B2 * | 11/2009 | Collazo | 606/87 |
| 7,682,362 B2 | 3/2010 | Dees, Jr. | |
| 8,734,453 B2 * | 5/2014 | Tuttle et al. | 606/87 |
| 2002/0173797 A1 | 11/2002 | Van Zile et al. | |
| 2003/0040752 A1 | 2/2003 | Kitchens | |
| 2003/0114659 A1 | 6/2003 | Brusin et al. | |
| 2003/0149378 A1 | 8/2003 | Peabody et al. | |
| 2003/0153924 A1 | 8/2003 | Kana et al. | |
| 2004/0039395 A1 | 2/2004 | Coon et al. | |
| 2005/0049603 A1 | 3/2005 | Calton et al. | |
| 2005/0143745 A1 * | 6/2005 | Hodorek et al. | 606/87 |
| 2005/0149042 A1 | 7/2005 | Metzger | |
| 2005/0203528 A1 | 9/2005 | Couture et al. | |
| 2005/0261696 A1 | 11/2005 | Overes et al. | |
| 2005/0273115 A1 | 12/2005 | Coon et al. | |
| 2006/0009854 A1 * | 1/2006 | Justin et al. | 623/20.15 |
| 2006/0173463 A1 * | 8/2006 | Dees, Jr. | 606/88 |
| 2006/0179979 A1 * | 8/2006 | Dees, Jr. | 81/9.2 |
| 2006/0241634 A1 * | 10/2006 | Tuttle et al. | 606/86 |
| 2007/0239167 A1 * | 10/2007 | Pinczewski et al. | 606/87 |
| 2008/0183178 A1 | 7/2008 | Collazo | |
| 2009/0204115 A1 | 8/2009 | Dees et al. | |
| 2010/0234850 A1 * | 9/2010 | Dees et al. | 606/87 |
| 2011/0213378 A1 * | 9/2011 | Dees, Jr. | 606/89 |
| 2012/0078262 A1 * | 3/2012 | Pinczewski et al. | 606/88 |
| 2012/0089145 A9 * | 4/2012 | Pinczewski et al. | 606/87 |
| 2013/0012941 A1 * | 1/2013 | Dees et al. | 606/62 |

OTHER PUBLICATIONS

Examiner's First Report for corresponding Australian Application No. 2006299438, mailed Sep. 8, 2011, 3 pages.

Office Action for corresponding Japanese Application No. 2008-534670, mailed Aug. 9, 2011, 4 pages.

Notice of Reasons for Rejection for Japanese Application No. 2008-534670, mailed Mar. 26, 2012.

Communication Pursuant to Article 94(3) EPC for European Application No. 06816263.5, mailed Jun. 6, 2013.

International Search Report and Written Opinion for International Application No. PCT/US2011/029321, mailed Nov. 25, 2011.

Femoral Anterior Stylus schematic described as 'Lock knob (threaded) which locks arm from all movement,' one page (1997).

Revision Tibial Stylus schematic, one page (2004).

Schematic described as 'Spring and nylon washer provide resistance to the stylus arm to provide resistance to translation, yet allows it when force is applied,' one page (2003).

Anterior Stylus Assembly schematic described as 'This stylus only allows rotation of the stylus arm around the connection axis,' one page (1996).

Notice of Allowance from U.S. Appl. No. 11/344,778 dated Nov. 6, 2009.

Examiner's Interview Summary Record from U.S. Appl. No. 11/344,778 dated Nov. 4, 2009.

Examiner's Interview Summary Record from U.S. Appl. No. 11/344,778 dated Nov. 2, 2009.

Office Action from U.S. Appl. No. 11/344,778 dated Aug. 17, 2009.
Office Action from U.S. Appl. No. 11/344,778 dated Mar. 3, 2009.
Office Action from U.S. Appl. No. 11/344,778 dated Dec. 8, 2008.

Examination Report issued in Canadian Application No. 2,624,644, on Mar. 18, 2013, 3 pages.

Patent Examination Report No. 1 for Australian Application 2013222044, mailed Oct. 8, 2014.

* cited by examiner

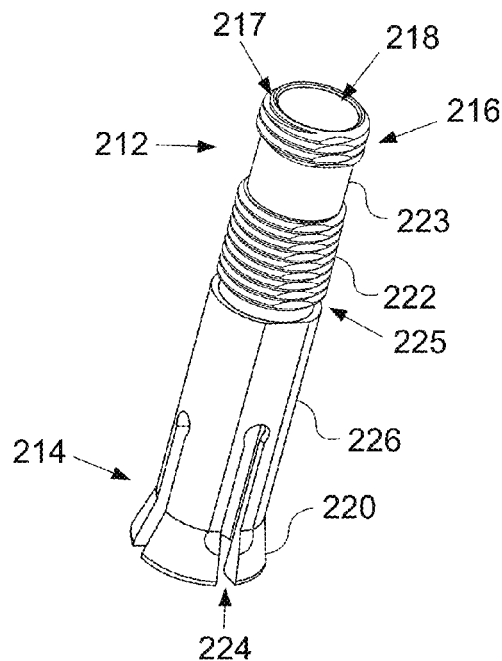
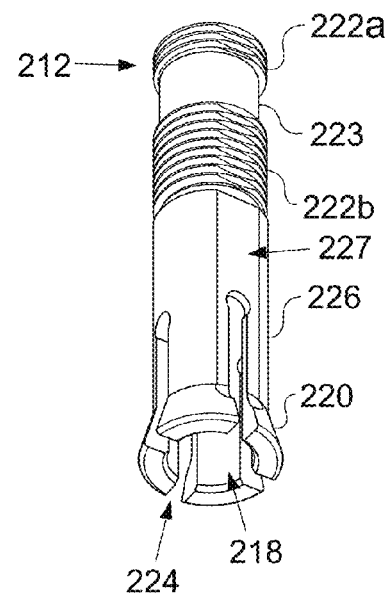
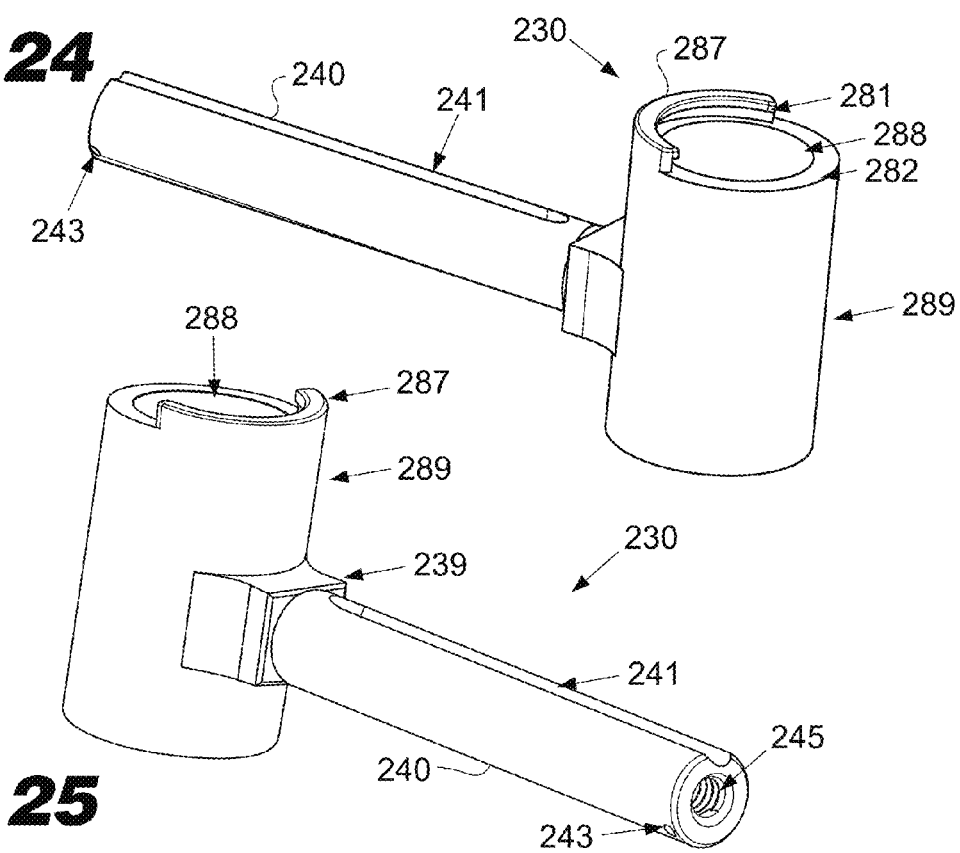

FIG. 35
FIG. 36
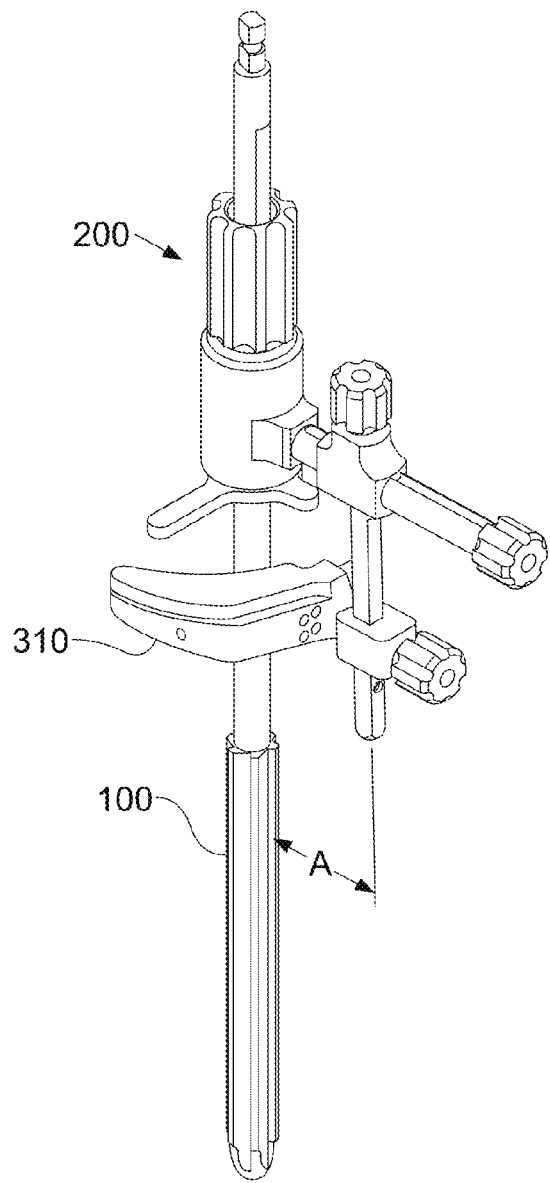
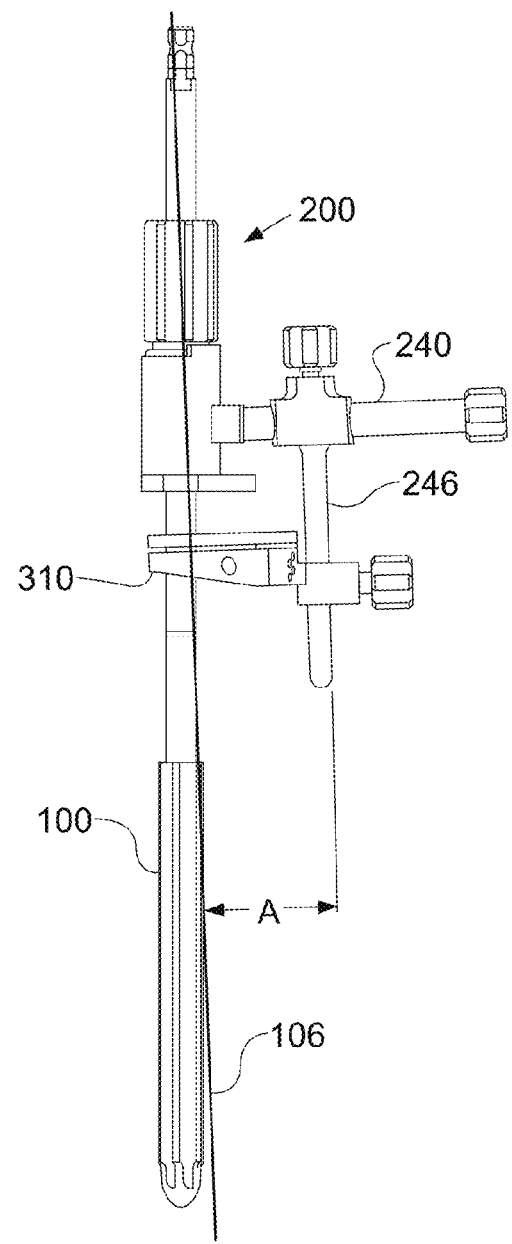

FIG. 56
FIG. 58
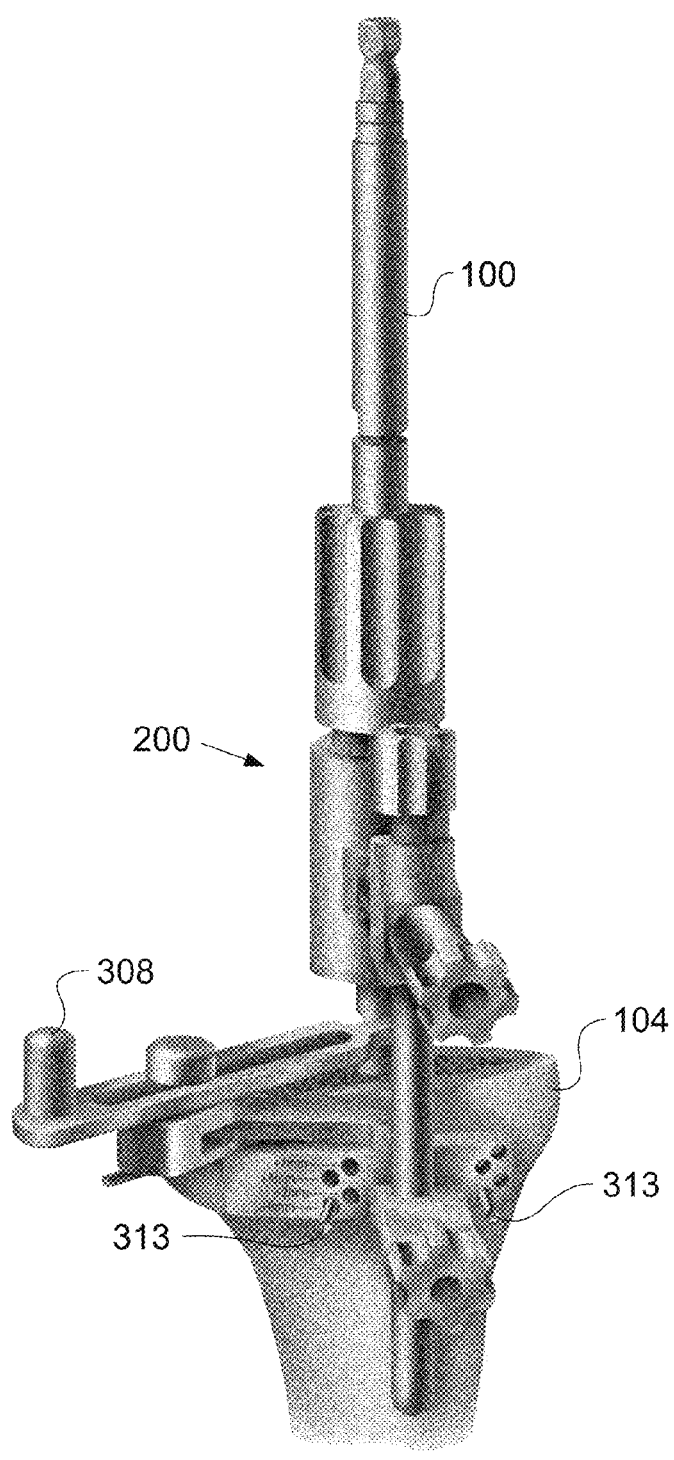
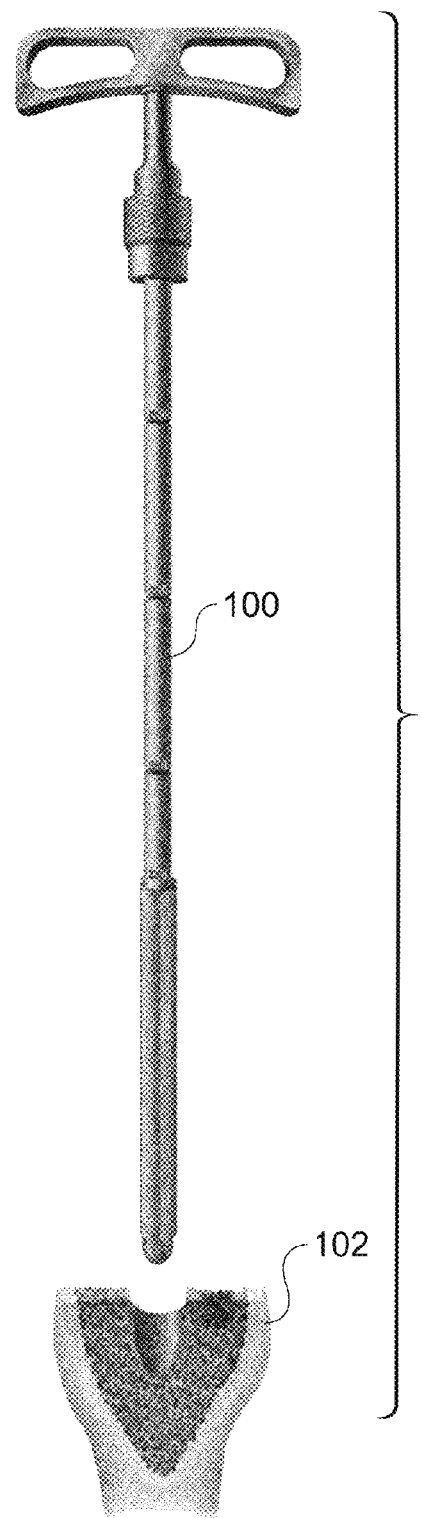

LOCKING INSTRUMENT ASSEMBLY

CROSS-REFERENCE TO RELATED APPLICATIONS

This application is a continuation of U.S. patent application Ser. No. 12/089,177, filed Aug. 25, 2008, now allowed, which is a U.S. National Stage Application of International Application No. PCT/US06/38859 filed Oct. 3, 2006, which claims the benefit of U.S. Provisional Application Ser. No. 60/723,228, filed Oct. 3, 2005 and U.S. Provisional Application Ser. No. 60/725,345, filed Oct. 11, 2005. The disclosure of each of the prior applications is incorporated by reference in its entirety.

BACKGROUND OF THE INVENTION

1. Field of the Invention

This invention relates generally to orthopaedic instrumentation and, more particularly, to orthopaedic cutting instruments.

2. Related Art

Most orthopedic instruments rely on bone spikes or pins for fixation. Other instruments use an intramedullary (IM) instrument with coupling configurations for the purpose of instrument correlation. However, these previous devices do not control all degrees of freedom. These previous devices are not stable nor are they relatively accessible.

Other instruments connect to a preset-length, intramedullary instrument through a threaded connection. This method restricts the amount of stability achieved to what is derived from the preset-length intramedullary instruments. If it were possible not to restrict the intramedullary instrument length, a surgeon could first stabilize the intramedullary instrument and then rigidly connect the correlating instrument to the intramedullary instrument.

Typically, the intramedullary or axial reference instrument(s) and/or the guide assembly are removed before resection because absent such removal the guide or instrument would interfere with the resection. Thus, the stability gained through the connection of the guide assembly and the axial reference instrument is typically lost.

The cutting plane and/or axis must be derived anatomically, usually through intramedullary referencing. However, in some instances, an alternative reference axis is utilized for unusual circumstances (i.e., deformities, trauma, disease, etc.). In either case, an instrument establishing a reference axis usually relative to a mechanical axis (i.e. intramedullary referencing) is rigidly fixed to/in bone. A cutting guide, with or without a guide assembly, is attached to this reference axis with a purpose of deriving a cutting plane and/or axis (i.e., posterior slope, valgus angle, etc.). The cutting guide is usually fixed to the bone using a bone spike(s), screw(s), drill(s) and/or pin(s). Normally, the reference axis and guide assembly are then removed for clearance for a cutting instrument.

There remains a need in the art for a device that can accurately establish rigid fixation of an instrument relative to an intramedullary reference axis. Further, there remains a need in the art for a modular device that allows for positioning of cutting guides and alignment guides relative to an intramedullary reference axis.

SUMMARY OF THE INVENTION

It is in view of the above problems that the present invention was developed. The invention is a locking instrument assembly for use in conjunction with an intramedullary device. The locking instrument assembly includes an inner collet, an intermediate body, and a knob. The inner collet has a first end portion, a second end portion, and a longitudinally extending inner bore. The first end portion has a collar, and the inner bore is adapted to receive the intramedullary device. The intermediate body has an inner portion and an outer portion. The inner portion is adapted to engage the collar. The knob is adapted to engage the intermediate body. As the knob engages the intermediate body, the intermediate body engages the collar such that the inner collet applies a clamping force to the intramedullary device.

In embodiments of the invention, the intermediate body is selected from the group consisting of an outer body and an orientation base.

In other embodiments of the invention, the second end portion has a fastener member, and the knob engages the fastener member.

In some embodiments of the invention, the knob has a flange, the intermediate body has a shoulder with a recess, and the recess receives the flange.

In embodiments of the invention, the inner collet has at least one relief area.

In other embodiments of the invention, the intermediate body has at least one relief area.

In some embodiments of the invention, the inner collet and the intermediate body have complimentary planar sections.

In embodiments of the invention, the locking instrument assembly also includes an offset collet handle base and an offset collet inner thread.

In embodiments of the invention, an instrument is attached to the intermediate body. The intermediate body may apply a clamping force to the instrument. The instrument may be selected from the group consisting of an anterior-posterior cutting block and a valgus alignment guide.

In some embodiments, a portion of the intermediate body is angled in order to angle the instrument relative to the intramedullary device.

In embodiments of the invention, the intermediate body is an orientation base, and the locking instrument assembly further comprises an outer body mounted on the orientation base.

In embodiments of the invention, the locking instrument assembly also includes a translation rod connected to the outer body. A rotation lock knob may be connected to the translation rod. A down rod may be connected to the translation rod. A translation lock knob may be connected to the down rod. A cutting guide may be connected to the down rod.

In other embodiments of the invention, the orientation base further comprises at least one notch and the rotation lock knob selectively engages the at least one notch.

In embodiments of the invention, the inner collet includes a base portion, and the inner bore is coaxial with the base portion.

In other embodiments of the invention, the inner collet includes a base portion, and a central axis of the inner bore is offset from a central axis of the base portion. A handle may be operatively connected to the inner collet.

In embodiments of the invention, the intermediate body of the locking instrument assembly provides a modular connection point for various instruments.

In embodiments of the invention, the locking instrument assembly may be adjusted axially and/or rotationally relative to the intramedullary device.

The invention has several advantages over prior devices and techniques. For example, by adding the ability to rotate the cutting guide on either a reference axis or an established secondary axis, the surgeon is able to maneuver the resection instrumentation around obstructions or clearance issues. By the ability to rotate the cutting guide around the second cutting axis, the removal of the reference axis prior to resection is not necessary. Therefore, primary fixation can be derived from the primary axis; reducing and/or eliminating the need for secondary fixation devices, such as bone spike(s), screw(s), drill(s) and/or pin(s).

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 22 is a top perspective view of the inner collet in a third embodiment;

FIG. 23 is a bottom perspective view of the inner collet shown in FIG. 22;

FIG. 24 is a front perspective view of the outer body in a third embodiment;

FIG. 25 is a rear perspective view of the outer body shown in FIG. 24;

FIG. 35 is a front perspective view of the second embodiment of the locking instrument assembly mounted on an intramedullary device;

FIG. 36 is a side view of the second embodiment shown in FIG. 35;

FIG. 56 is a front perspective view of the locking instrument assembly as mounted on the intramedullary device;

FIG. 58 is a front view of an intramedullary device and a femur;

DETAILED DESCRIPTION OF THE EMBODIMENTS

Figure 1:
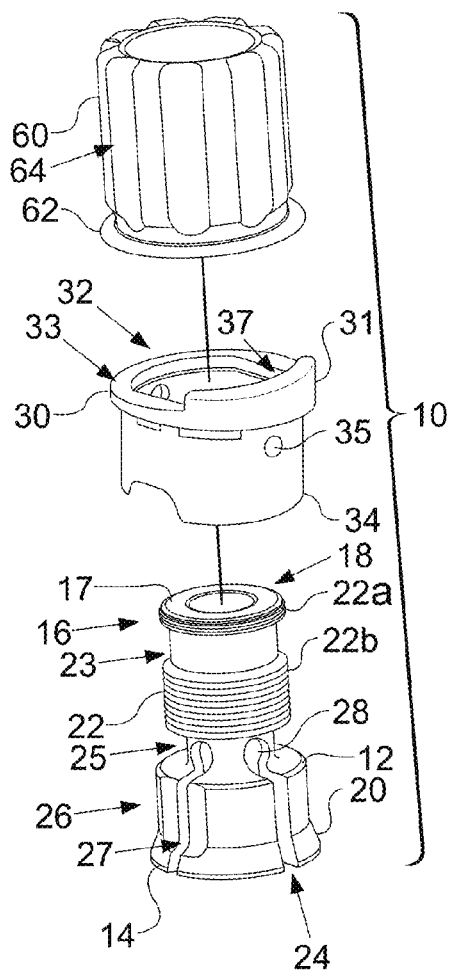
FIG. 1 is an exploded perspective view of a locking instrument assembly in a first embodiment.

Referring to the accompanying drawings in which like reference numbers indicate like elements, FIG. 1 illustrates a locking instrument assembly 10. The locking instrument assembly 10 may be used in conjunction with an intramedullary device 100, such as an intramedullary nail, intramedullary reamer, or trial stem. The assembly 10 includes an inner collet 12, an outer body 30, and a knob 60.

The inner collet 12 has a first end portion 14, a second end portion 16, and a longitudinally extending inner bore 18. The first end portion 14 has a collar 20 and a base portion 26. The base portion 26 may include one or more planar sections 27. In the embodiment depicted in FIG. 1, the inner collet has two planar sections 27 that are substantially parallel to one another. The base portion 26 may be cylindrical, oval, or cylindrical with tangent portions removed. In the depicted embodiment, the base portion 26 is generally cylindrical, and the inner bore 18 is substantially coaxial with the base portion 26.

Inner collet 12 functions as a collet or wedge. The collar 20 may include one or more relief areas 24. The relief areas 24 allow a portion of the inner bore 18 to at least partially collapse. In the embodiment depicted in FIG. 1, the collar 20 has four equally spaced relief areas 24 about its circumference. In some embodiments, the relief area 24 has a rectangular shape and terminates in a hole 28. The second end portion 16 has a fastener member 22. In the embodiment depicted in FIG. 1, the fastener member 22 is a helical groove or thread, but those of ordinary skill in the art would understand that other types of fastening mechanisms may be used. For example, the fastener member 22 may be a pin that engages a cam slot of the outer body 30. The fastener member 22 may extend from the base portion 26 to an inner collet face 17, but in the depicted embodiment the inner collet 12 includes a first cylindrical portion 23 and a second cylindrical portion 25 which separate a first fastener member portion 22a and a second fastener member portion 22b from one another and from the base 26. The inner bore 18 is adapted to receive the intramedullary device 100. In other words, the inner bore 18 is shaped to fit the intramedullary device 100.

The outer body 30 has a shoulder 31, an inner portion 32, a face 33 and an outer portion 34. The outer body 30 may be cylindrical, oval, or elliptical in shape. The inner portion 32 is shaped and dimensioned to receive the inner collet 12 and particularly the base portion 26. In some embodiments, the outer body 30 includes one or more instrument mounting holes 35. The inner portion 34 is adapted to engage the collar 20 when the outer body 30 is placed over the inner collet 12. The knob 60 engages the face 33, and the shoulder 31 projects from the face 33. In some embodiments, the knob 60 has a flange 62, and the shoulder 31 has a recess that receives a portion of the flange 62. In some embodiments, the face 33 is substantially perpendicular to a central axis of the inner bore 18, but in other embodiments, the face 33 may be angled from about one to about ten degrees to adjust the valgus angle of an instrument. In the depicted embodiment, the face 33 is angled from about four to about seven degrees. The outer body 30 may include one or more base engagement portions 37. The base engagement portions 37 are adapted to mate with the planar sections 27. In the depicted embodiments, the base engagement portions 37 are substantially planar.

The knob 60 is adapted to mate with the fastener member 22 and engage the outer body 30, wherein as the knob 60 mates with the fastener member 22, the outer body 30 engages the collar 20 such that the inner collet 12 applies a clamping force to the intramedullary device 100. The knob 60 is removably attached to the outer body 30 to pull the outer body 30 upwardly and away from the collar 20 in order to remove the clamping force. As noted above, some embodiments of the knob 60 include the flange 62 which is received by a recess of the shoulder 31. The flange 62 engages the shoulder 31 to pull the outer body 30 upwardly and away from the collar 20 in order to remove the clamping force. Alternatively, the knob 60 may be pinned to the outer body 30. In some embodiments, the knob 60 includes one or more longitudinal grooves 64. The longitudinal grooves 64 aid a user in gripping the knob 60.

The locking instrument assembly 10 is assembled by inserting inner collet 12 through outer body 30 and then threading the knob 60 on to inner collet 12. If the knob 60 includes the flange 62, then a first step would be to engage the flange 62 with the recess of the shoulder 31 and then insert the inner collet 12 through outer body 30.

Outer body 30 is used as a modular connector. Thus, an instrument, such as a cutting guide or an alignment block, may be attached to the outer body 30. In an alternative embodiment, an instrument may substitute directly for the outer body 30. Thus, in this alternative embodiment, an instrument that has the same characteristics as the outer body 30 is placed over the inner collet 12 and locked into place as the knob 60 tightens against the inner collet 12.

Figure 2:
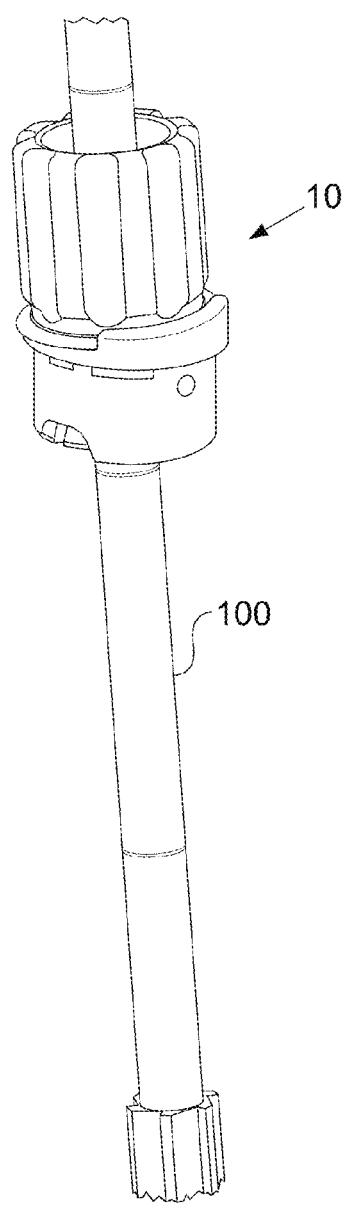
FIG. 2 is a perspective view of the locking instrument assembly as mounted on an intramedullary device.

Referring now to FIG. 2, the intramedullary device 100 is rigidly fixed in a bone. The locking instrument assembly 10 is assembled but without tightening the knob 60. After rigid fixation of the intramedullary device 100, the pre-assembled locking instrument assembly 10 is slid over the intramedullary device 100. The locking instrument assembly 10 is located axially in the desired position along the intramedullary device 10. The knob 60 is turned to tighten and wedge the outer body 30 against the inner collet 12. The collar 20 collapses slightly to apply a clamping force and grip the intramedullary device 100. After the outer body 30 is locked in place, any number of various instruments may be attached to the outer body 30. Thus, outer body 30 provides a rigid connection point for connecting any number of instruments to a rigidly connected intramedullary device 100.

Figure 3:
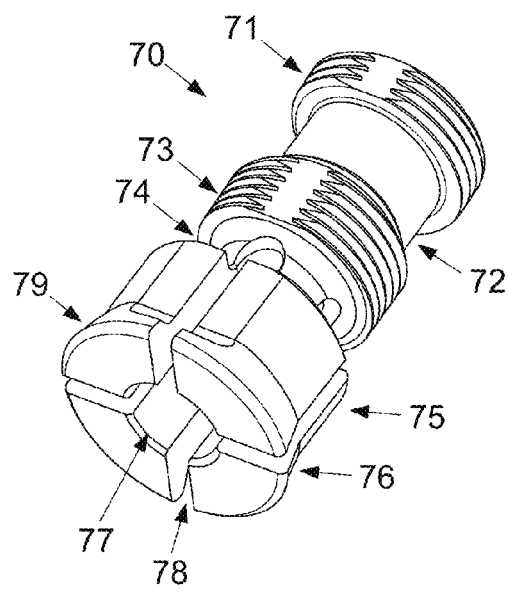
FIG. 3 is a bottom perspective view of an inner collet in a second embodiment.
Figure 4:
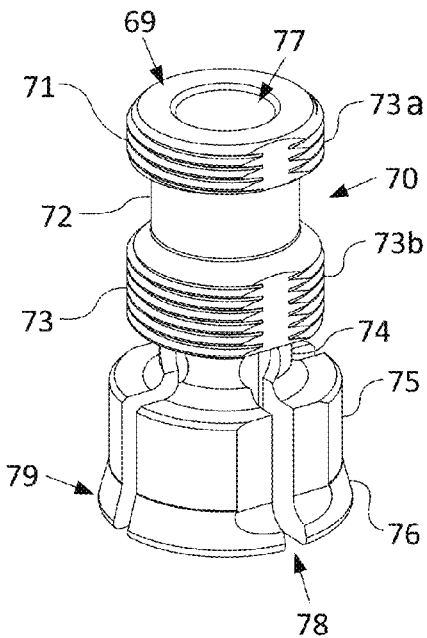
FIG. 4 is a top perspective view of the inner collet shown in FIG. 3.

FIGS. 3 and 4 illustrate a second embodiment of the inner collet. The inner collet 70 includes a first end portion 76, a second end portion 71, and a longitudinally extending inner bore 77. The first end portion 76 has a collar 79 and a base portion 75. The base portion 75 may be cylindrical, oval, or cylindrical with tangent portions removed. In the depicted embodiment, the base portion 75 is generally cylindrical, and the inner bore 77 is substantially coaxial with the base portion 75.

Inner collet 70 functions as a collet or wedge. The collar 79 may include one or more relief areas 78. The relief areas 78 allow a portion of the inner bore 77 to at least partially collapse. In some embodiments, the relief area 24 has a keyhole shape. The second end portion 71 has a fastener member 73. In the embodiment depicted in FIG. 3, the fastener member 73 is a helical groove or thread, but those of ordinary skill in the art would understand that other types of fastening mechanisms may be used. The fastener member 73 may extend from the base portion 75 to an inner collet face 69, but in the depicted embodiment the inner collet 70 includes a first cylindrical portion 72 and a second cylindrical portion 74 which separate a first fastener member portion 73a and a second fastener member portion 73b from one another and from the base 75. The inner bore 77 is adapted to receive the intramedullary device 100. In other words, the inner bore 77 is shaped to fit the intramedullary device 100.

Figure 5:
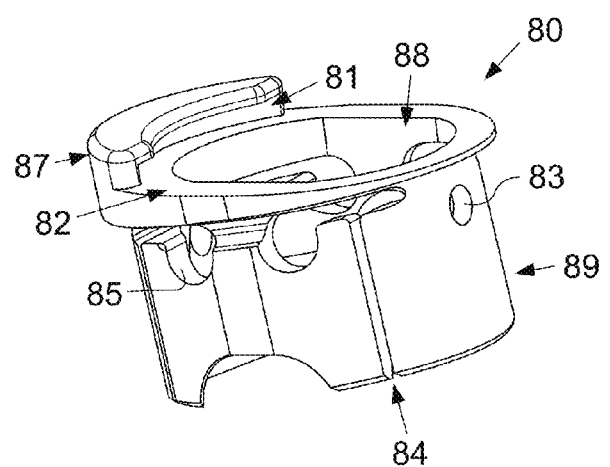
FIG. 5 is a front perspective view of an outer body in a second embodiment.
Figure 6:
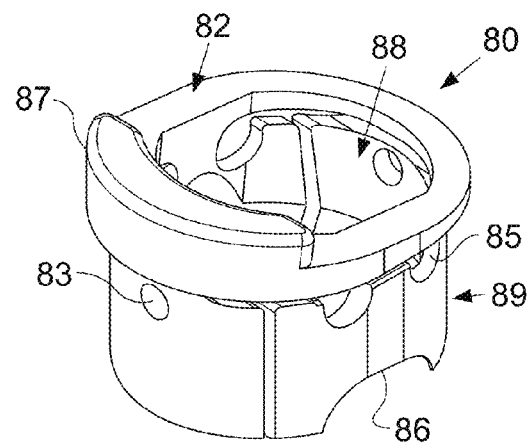
FIG. 6 is a top perspective view of the outer body shown in FIG. 5.
Figure 7:
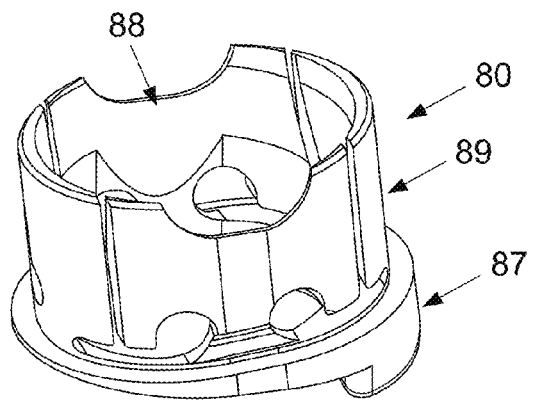
FIG. 7 is a bottom perspective view of the outer body shown in FIG. 5.
Figure 10:
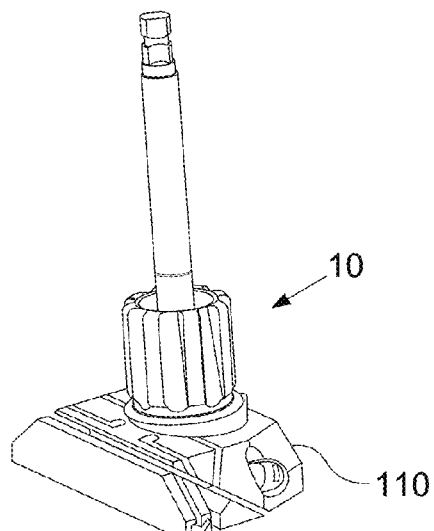
FIG. 10 is a front perspective view of a first instrument attached to the locking instrument assembly.

FIGS. 5, 6, and 7 illustrate a second embodiment of the outer body. The outer body 80 has a shoulder 87, an inner portion 88, a face 82 and an outer portion 89. The outer body 80 may be cylindrical, oval, or elliptical in shape. The inner portion 88 is shaped and dimensioned to receive the inner collet 12, 70 and particularly the base portion 26, 75. In some embodiments, the outer body 80 includes one or more instrument mounting holes 83. The inner portion 88 is adapted to engage the collar 20, 79 when the outer body 80 is placed over the inner collet 12, 70. The knob 60 engages the face 82, and the shoulder 87 projects from the face 82. In some embodiments, the knob 60 has a flange 62, and the shoulder 87 has a recess 81 that receives a portion of the flange 62. In some embodiments, the face 82 is substantially perpendicular to a central axis of the inner bore 18, 77, but in other embodiments, the face 82 may be angled from about one to about ten degrees relative to the central axis to adjust the valgus angle of an instrument. In the depicted embodiment, the face 82 is angled from about four to about seven degrees. The outer body 80 may include one or more first relief areas 84 and one or more second relief areas 85. The relief areas 84, 85 allow the outer body 80 to expand as it is pressed against the collar 20, 79. In this manner, the locking instrument assembly 10 is dual locking First, as the outer body 80 is pressed against the collar 20, 79, the inner collet 12, 70 at least partially collapses to lock the inner collet 12, 70 relative to the intramedullary device. Second, as the outer body 80 presses against the collar 12, 70, the outer portion 89 expands. As is explained in greater detail below, when an instrument is connected to the outer portion 89, this expansion locks the outer body 80 to the instrument. This expansion of the outer portion 89 prevents the instrument from moving axially and/or rotationally relative to the outer body 80. The outer body 80 also may include one or cutouts 86. The cutouts 86 are used to remove sharp edges.

Figure 8:
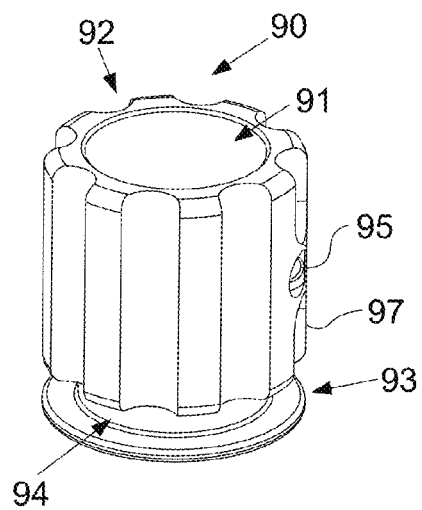
FIG. 8 is a top perspective view of a knob in a second embodiment.
Figure 9:
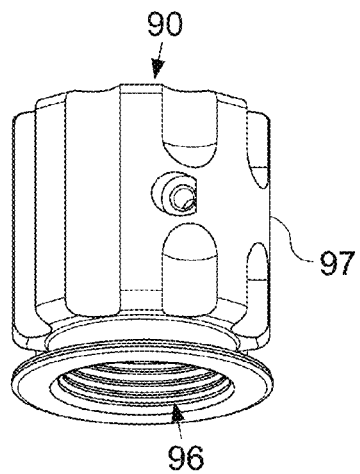
FIG. 9 is a bottom perspective view of the knob shown in FIG. 8.
Figure 11:
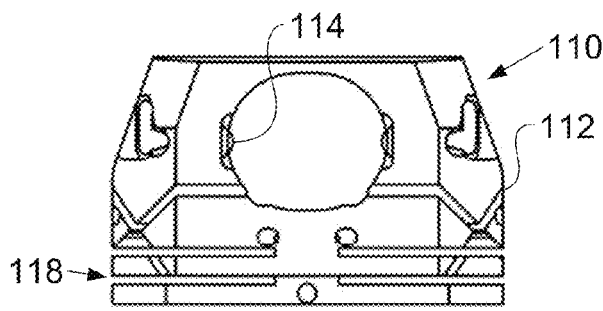
FIG. 11 is a top view of the first instrument shown in FIG. 10.
Figure 12:
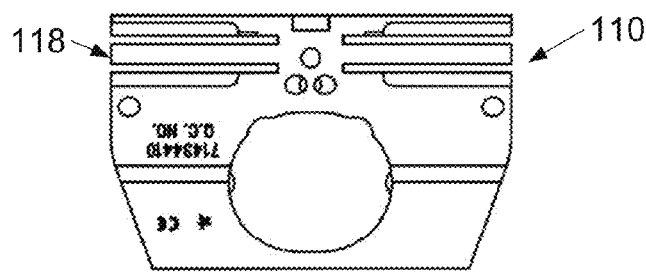
FIG. 12 is a bottom view of the first instrument shown in FIG. 10.
Figure 13:
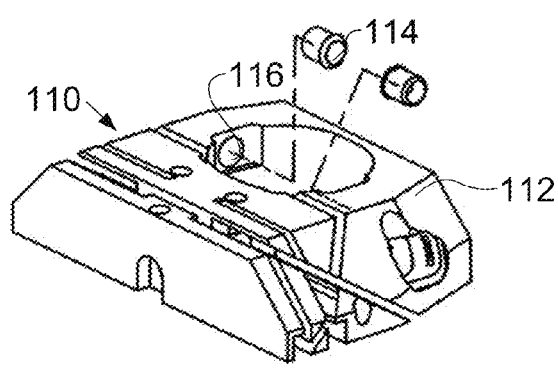
FIG. 13 is an exploded perspective view of the first instrument shown in FIG. 10.

FIGS. 8 and 9 illustrate a second embodiment of the knob. The knob 90 is adapted to mate with the fastener member 22, 73 and engage the outer body 30, 80, wherein as the knob 90 mates with the fastener member 22, 73, the outer body 30, 80 engages the collar 20, 79 such that the inner collet 12 applies a clamping force to the intramedullary device 100. The knob 90 is removably attached to the outer body 30, 80 to pull the outer body 30, 80 upwardly and away from the collar 20, 79 in order to remove the clamping force. Some embodiments of the knob 90 include a flange 93 which is received by the recess 81 of the shoulder 87. The flange 93 engages the shoulder 31, 87 to pull the outer body 30, 80 upwardly and away from the collar 20, 79 in order to remove the clamping force. Alternatively, the knob 90 may be pinned to the outer body 30, 80. In some embodiments, the knob 90 includes one or more longitudinal grooves 92. The longitudinal grooves 92 aid a user in gripping the knob 90. The knob 90 includes an inner bore 91. At least a portion of the inner bore 91 is threaded and includes threads 96. The inner bore 91 is sized to receive the inner collet 12, 70, and the threaded portion 96 is adapted to mate with the fastener member 22, 73. In some embodiments, the knob 90 includes a pin hole 95. In some embodiments, a spring pin (not shown) is inserted into the pin hole 95 to retain the inner collet 12, 70 to the knob 90. The knob 90 also includes the third cylindrical portion 94. The knob 90 includes a main body 97, and the third cylindrical portion 94 distally spaces the flange 93 away from the main body 97.

The locking instrument assembly 10 is assembled to any number of various instruments without tightening the knob 60, 90. Thus, outer body 30, 80 provides a rigid connection point for connecting any number of instruments to a rigidly connected intramedullary device 100. This is significant as modularity can reduce the time necessary for surgery and can reduce the costs of manufacturing. The pre-assembled locking instrument assembly 10 is slid over the intramedullary device 100. The locking instrument assembly 10 is located axially in the desired position along the intramedullary device 10. The knob 60, 90 is turned to tighten and wedge the inner collet 12, 70 against the outer body 30, 80. The collar 20 collapses slightly to apply a clamping force and grip the intramedullary device 100. In some embodiments, the knob 60, 90 continues to be tightened to wedge the outer body 80 against any of the various instruments and thereafter rigid fixation of the intramedullary device 100 is achieved. Thus, this last embodiment locks against both the intramedullary device and against the instrument.

FIGS. 10, 11, 12 and 13 illustrate a first instrument 110 attached to the locking instrument assembly 10. In the depicted embodiments, the first instrument 110 is an anterior-posterior cutting block assembly. The first instrument 110 includes an anterior-posterior cutting block 112 and at least one plunger 114. The anterior-posterior cutting block 112 includes at least one slot 118 and at least one plunger hole 116. The at least one plunger hole 116 receives the at least one plunger 114. In the depicted embodiments, the at least one plunger 114 is press-fit into the at least one plunger hole 116. The anterior-posterior cutting block 112 also includes an outer body hole 120. The outer body hole 120 is shaped and dimensioned to receive the outer body 30, 80. As such, the at least one plunger 114 is adapted to engage the instrument mounting hole 35, 83. As noted above, the outer body 80 is adapted to expand as the outer body 80 engages the collar 20, 79. Thus, the outer body 80 may expand to engage the outer body hole 120 of the first instrument 110. The engagement of the expanding outer body 80 with the outer body hole 120 prevents or substantially reduces the likelihood that the first instrument 110 will rotate or move axially after the inner collet 12, 70 locks against the intramedullary device 100.

FIGS. 14, 15, 16, 17, 18, 19, and 20 illustrate a second instrument 150 attached to the locking instrument assembly 10. In the depicted embodiments, the second instrument 150 is a valgus guide assembly. The second instrument 150 includes a first portion 152 and a second portion 156. The second portion 156 is removably attached to the first portion 152. The first portion 152 includes a valgus guide collet block 153 and an alignment guide frame sub-assembly 154. The valgus guide block 153 is removably attached to the alignment guide frame sub-assembly 154. The valgus guide block 153 includes plungers 151. The alignment guide frame sub-assembly 154 includes plungers 155. The second portion 156 includes a distal femoral cutting block assembly 157 and a block knob 158. In some embodiments, the second portion 156 includes a spring pin 159 to retain the block knob 158 to the distal femoral cutting block assembly 157. The first portion 152 includes an outer body mounting hole 160. As noted above, the outer body 80 is adapted to expand as the outer body 80 engages the collar 20, 79. Thus, the outer body 80 may expand to engage the outer body hole 160 of the first portion 152. The engagement of the expanding outer body 80 with the outer body hole 160 prevents or substantially reduces the likelihood that the second instrument 150 will rotate or move axially after the inner collet 12, 70 locks against the intramedullary device 100.

Figure 21:
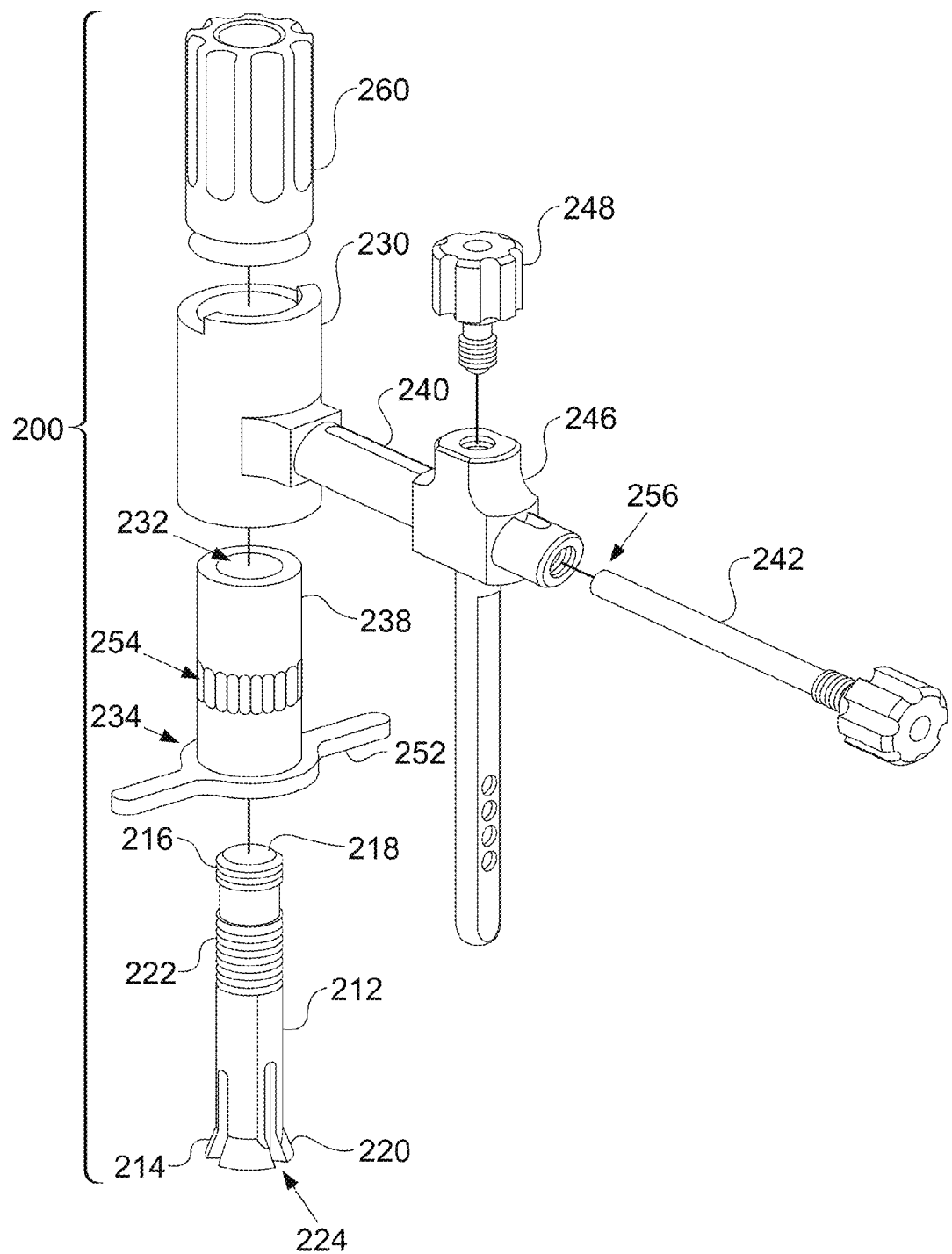
FIG. 21 is an exploded perspective view of the locking instrument assembly in a second embodiment.

FIG. 21 illustrates a second embodiment of the locking instrument assembly. FIG. 21 illustrates a locking instrument assembly 200. The locking instrument assembly 200 may be used in conjunction with the intramedullary device 100, such as an intramedullary nail, intramedullary reamer, or trial stem. The assembly 200 includes an inner collet 212, an outer body 230, an orientation base 238, and a knob 260.

A translation rod 240 is connected to the outer body 230. The translation rod receives a rotation lock knob 242. A down rod 246 is connected to the translation rod 240. A translation lock knob 248 is connected to the down rod 246. The locking instrument assembly 200 is further assembled by connecting the translation rod 240 to the outer body 230. As an example, the translation rod 240 may be welded to the outer body 230. The down rod 246 is oriented and slid over the translation rod 240. Then, the rotation lock knob 242 is threaded into the translation rod 240. The translation lock knob 248 is threaded into the down rod 246.

FIGS. 22 and 23 illustrate the inner collet 212. The inner collet 212 has a first end portion 214, a second end portion 216, and a longitudinally extending inner bore 218. The first end portion 214 has a collar 220 and a base portion 226. The base portion 226 may include one or more planar sections 227. In the embodiment depicted in FIG. 23, the inner collet has two planar sections 27 that are substantially parallel to one another. The base portion 226 may be cylindrical, oval, or cylindrical with tangent portions removed. In the depicted embodiment, the base portion 226 is generally cylindrical, and the inner bore 218 is substantially coaxial with the base portion 226.

Inner collet 212 functions as a collet or wedge. The collar 220 may include one or more relief areas 224. The relief areas 224 allow the collapse of a portion of the inner bore 218. In the embodiment depicted in FIG. 23, the collar 220 has four equally spaced relief areas 224 about its circumference. The relief areas 224 may be rectangular, prolated, or key hole shaped. The second end portion 216 has a fastener member 222. In the embodiment depicted in FIG. 22, the fastener member 222 is a helical groove or thread, but those of ordinary skill in the art would understand that other types of fastening mechanisms may be used. The fastener member 222 may extend from the base portion 226 to an inner collet face 217, but in the depicted embodiment the inner collet 212 includes a first cylindrical portion 223 and a second cylindrical portion 225 which separate a first fastener member portion 222a and a second fastener member portion 222b from one another and from the base 226. The inner bore 218 is adapted to receive the intramedullary device 100. In other words, the inner bore 218 is shaped to fit the intramedullary device 100.

FIGS. 24 and 25 illustrate the outer body 230. The outer body 230 has a shoulder 287, an inner portion 288, a face 282 and an outer portion 289. The outer body 230 may be cylindrical, oval, or elliptical in shape. The inner portion 288 is shaped and dimensioned to receive the inner collet 12, 70, 212 and particularly the base portion 26, 75, 226. The inner portion 288 is shaped and dimensioned to receive the orientation base 238. In some embodiments, the knob 260 has a flange 262, and the shoulder 287 has a recess 281 that receives a portion of the flange 262. In some embodiments, the face 282 is substantially perpendicular to a central axis of the inner bore 18, 77, 218, but in other embodiments, the face 282 may be angled from about one to about ten degrees relative to the central axis to adjust the valgus angle of an instrument. In the depicted embodiment, the face 282 is substantially perpendicular to the inner bore 18, 77, 218.

The translation rod 240 is connected to the outer body 230. In the embodiment depicted in FIGS. 24 and 25, the translation rod 240 is threaded into a boss 239, which is welded to the outer portion 289. The translation rod 240 includes a longitudinally extending slot 241. As explained in greater detail below, the longitudinally slot 241 is used to orient the down rod 246. The translation rod 240 is tubular and is at least partially threaded on inner end portion 245. In some embodiments, the translation rod 240 includes a pin mounting hole 243.

Figure 26:
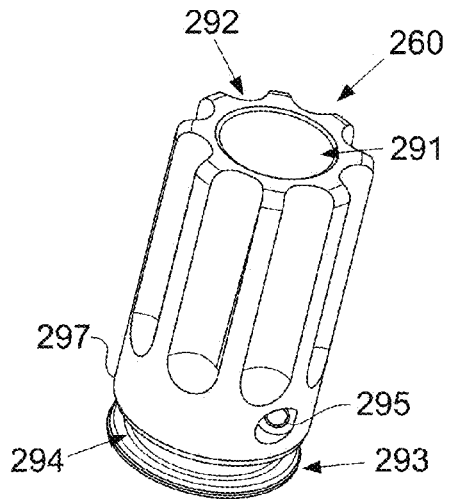
FIG. 26 is a top perspective view of the knob in a third embodiment.
Figure 27:
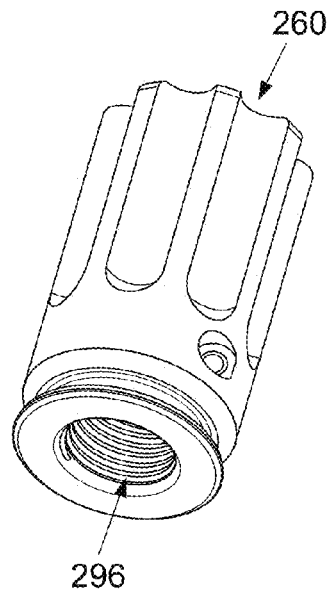
FIG. 27 is a bottom perspective view of the knob shown in FIG. 26.

FIGS. 26 and 27 illustrate the knob 260. The knob 260 is adapted to mate with the fastener member 222 and engage the orientation base 238, wherein as the knob 260 mates with the fastener member 222, the orientation base 238 engages the collar 220 such that the inner collet 212 applies a clamping force to the intramedullary device 100. The knob 260 is removably attached to the outer body 230 to pull the outer body 230 upwardly and away from the orientation base 238. Some embodiments of the knob 260 include a flange 293 which is received by the recess 281 of the shoulder 287. The flange 293 engages the shoulder 287 to pull the outer body 230 upwardly. Alternatively, the knob 90 may be pinned to the outer body 30, 80. In some embodiments, the knob 260 includes one or more longitudinal grooves 292. The longitudinal grooves 292 aid a user in gripping the knob 260. The knob 260 includes an inner bore 291. At least a portion of the inner bore 291 is threaded and includes threads 296. The inner bore 291 is sized to receive the inner collet 212, and the threaded portion 296 is adapted to mate with the fastener member 222. In some embodiments, the knob 260 includes a pin hole 295. In some embodiments, a spring pin (not shown) is inserted into the pin hole 295 to retain the inner collet 212 to the knob 260. The knob 260 also includes the third cylindrical portion 294. The knob 260 includes a main body 297, and the third cylindrical portion 294 distally spaces the flange 293 away from the main body 297.

Referring once again to FIG. 21, the orientation base 238 has an inner portion 232 and an outer portion 234. The inner portion 232 is adapted to engage the collar 220 when the orientation base 238 is placed over the inner collet 212. The knob 260 engages the orientation base, and the orientation base 238 pushes against the collar 220 to at least partially collapse the inner collet 212 such that the inner collet 212 exerts a clamping force on the intramedullary device 100. The orientation base 238 includes ears 252 and notches 254. In some embodiments, the axis of the inner diameter of the orientation base 238 is not coaxial with the outer diameter, and the ears 252 may be used to indicate an angle of the orientation base relative to the central axis of the inner bore 218. The notches 254 are spaced about the circumference of the outer portion 234. As explained in greater detail below, the notches 254 receive a tip portion 256 of the rotation lock knob 242.

Figure 28:
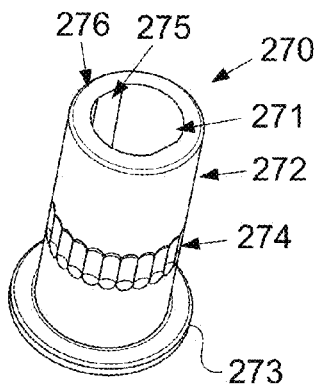
FIG. 28 is a top perspective view of the orientation base in a second embodiment.

FIG. 28 illustrates a second embodiment of the orientation base. The orientation base 270 includes an inner portion 271, an outer portion 272, a lip 273, one or more notches 274, and a face 276. The inner portion 271 may include one or more first planar walls 275. The first planar walls 275 are adapted to mate with the planar sections 227. When the locking instrument assembly 200 is assembled, the lip 273 engages the outer body 230. The notches 274 are spaced about the circumference of the outer portion 272. As explained in greater detail below, the notches 274 receive the tip portion 256 of the rotation lock knob 242. The face 276 is selectively engaged with the knob 260. In other words, as the knob 260 threads onto the inner collet 212, the knob 260 also engages the face 276.

Figure 29:
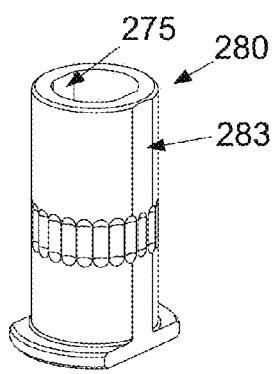
FIG. 29 is a top perspective view of the orientation base in a third embodiment.
Figure 30:
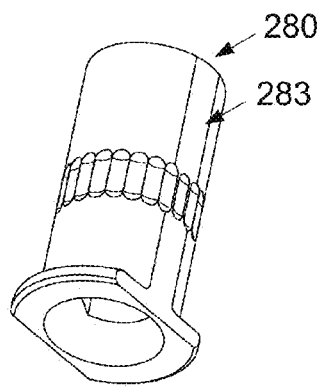
FIG. 30 is a bottom perspective view of the orientation base shown in FIG. 29.

FIGS. 29 and 30 illustrate a third embodiment of the orientation base. The orientation base 280 is similar to the second embodiment except the third embodiment includes second planar walls 283. The second planar walls 283 are substantially parallel to the first planar walls 275 and provide an indication as to orientation of the orientation base 280.

Figure 31:
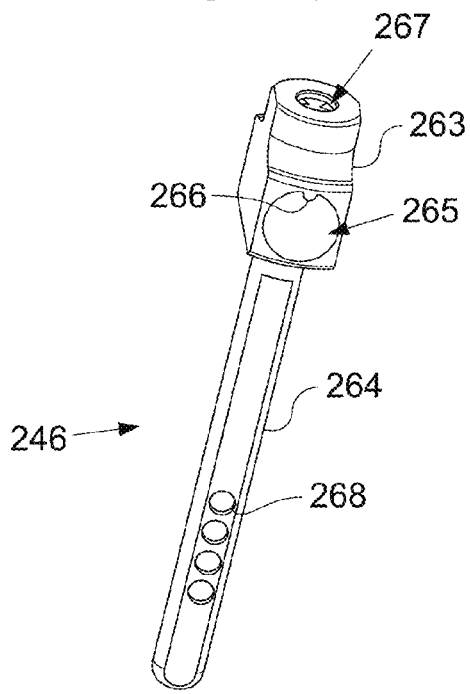
FIG. 31 is a front perspective view of a down rod.
Figure 32:
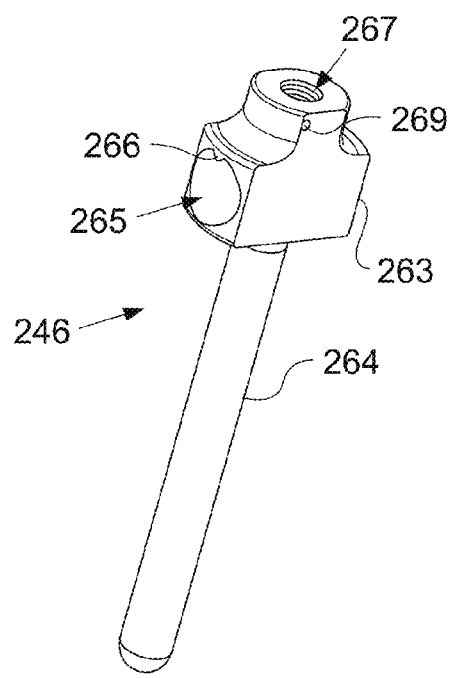
FIG. 32 is a side perspective view of the down rod shown in FIG. 31.

FIGS. 31 and 32 illustrate the down rod 246. The down rod 246 includes a block member 263 and a post 264. The post 264 is operatively connected to the block member 263. The block member 263 includes an opening 265. The opening 265 is shaped and dimensioned to mate with the translation rod 240. In some embodiments, the block member 263 includes key 266. The key 266 fits within the longitudinally extending slot 241 to provide an orientation to the down rod 246. The block member 263 also includes aperture 267. The aperture 267 receives the translation lock knob 248. In some embodiments, the aperture 267 is threaded. The post 264 may include locators 268. The locators 268 are cylindrical depressions that provide a positive stop for an instrument, such as a cutting block. The locators 268 are evenly spaced apart. In the embodiment depicted in FIG. 31, the locators 268 are spaced apart by about five millimeters. In some embodiments, the block member 263 includes pin hole 269. A spring pin (not shown) may be inserted into the pin hole 269 after the translation lock knob 248 is inserted into the aperture 267 in order to retain the translation lock knob 248.

Figure 33:
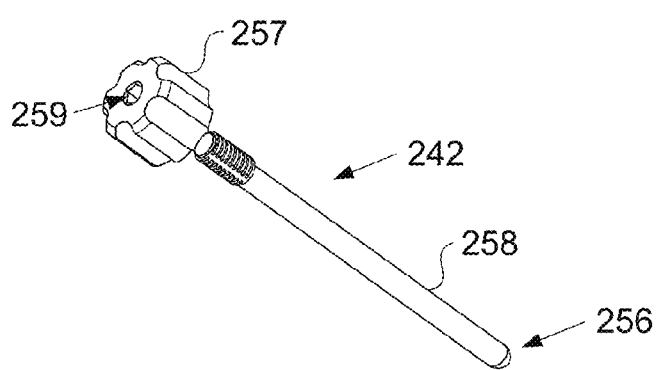
FIG. 33 is a front perspective view of a rotation lock knob.
Figure 34:
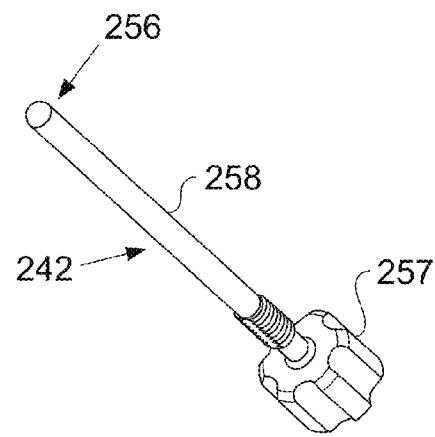
FIG. 34 is a rear perspective view of the rotation lock knob shown in FIG. 33.

FIGS. 33 and 34 illustrate the rotation lock knob 242. The rotation lock knob 242 includes a knob portion 257 and a rod portion 258. The knob portion 257 may include a fastener driver receiver 259. The fastener driver receiver 259 receives a fastener driver (not shown), which may be used to tighten the rotation lock knob 242. In the depicted embodiments, the fastener driver receiver 259 is hex shaped. A portion of the rod portion 257 may be threaded. The rod portion 258 also includes the tip portion 256. The tip portion 256 may be used to engage the notch 254, 274.

The locking instrument assembly 200 is assembled by inserting inner collet 212 through the orientation base, through the outer body 230 and then threading the knob 260 on to inner collet 212. Outer body 230 is used as a modular connector. Thus, an instrument, such as a cutting guide or an alignment block, may be attached to the outer body 230. In an alternative embodiment, an instrument may substitute directly for the outer body 230. Thus, in this alternative embodiment, an instrument that has the same characteristics as the outer body 230 is placed over the orientation base 238, 270, 280 and locked into place axially as the knob 260 tightens against the inner collet 212.

In a method of use, the locking instrument assembly 200 is slid over the intramedullary device 100, then the knob 260 is tightened onto the inner collet 212 pulling the inner collet 212 into the orientation base 238, 270, 280 causing a wedge effect between the inner collet 212 and the intramedullary device 100. Optionally, the rotation lock knob 242 is loosened or tightened to facilitate rotational freedom or constraint of the cutting guide/plane around the orientation base 238, 270, 280. The translation lock knob 248 is loosened or tightened to facilitate translational freedom or constraint of the cutting guide/plane along the translation rod 240.

In the instance shown, the knob 260 pulls the inner collet 212 with the use of threads creating a wedge effect between the intramedullary device 100 and the inner collet 212. This action locks all degrees of freedom of the orientation base with respect to the intramedullary device 100. The outer body 230 only has rotational freedom around the orientation base 238, 270, 280 because it is constrained axially by the orientation base 238, 270, 280 and the knob 260. The orientation base 238, 270, 280 dictates/determines the cutting axis that can be collinear to or at an angle to the intramedullary device 100. This cutting axis is maintained/translated through the connections of the outer body, the translation rod 240, and the down rod 246. The down rod 246 is where a cutting guide is attached.

The translation lock knob 248 is used to lock the down rod 246 from translation on the translation rod 240. The rotation lock knob 242 is used to lock rotation of the outer body 230, the translation rod 240, the down rod 246 and the cutting guide on the cutting axis or the orientation base 238, 270, 280. Notches 254, 274 around the central circumference of the orientation base 238, 270, 280 are to provide a positive stop location for the rotation lock knob 242.

FIGS. 35 and 36 illustrate the locking instrument assembly 200 as mounted on the intramedullary device 100. A tibia cutting block assembly 310 is mounted on the down rod 246. FIGS. 35 and 36 also illustrate a reference axis 106. An angle A of the down rod 246 is measured from this reference axis. The angle A may vary from zero degrees to about ten degrees. Because the tibia cutting block assembly 310 is mounted to the down rod 246, the angle A indicates a slope of the resection plane. It may be desirable in some instances to adjust the slope of the resection plane when using the tibia cutting block assembly 310. This may be accomplished in several ways. First, as noted above, the orientation base 238 may have an outside diameter that is angled relative to the inside diameter. Second, the translation rod 240 may be angled relative to the outer body 230. Third, the down rod 246 may be angled relative to the translation rod 240. However, in the embodiments depicted in FIGS. 35 and 36, the down rod 246 is substantially parallel to the intramedullary device 100.

Figure 37:
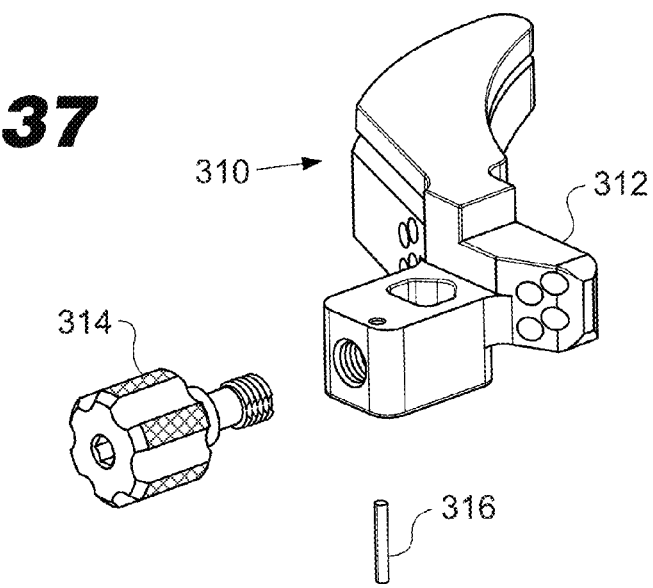
FIG. 37 is an exploded view of a tibia cutting block assembly.
Figure 38:
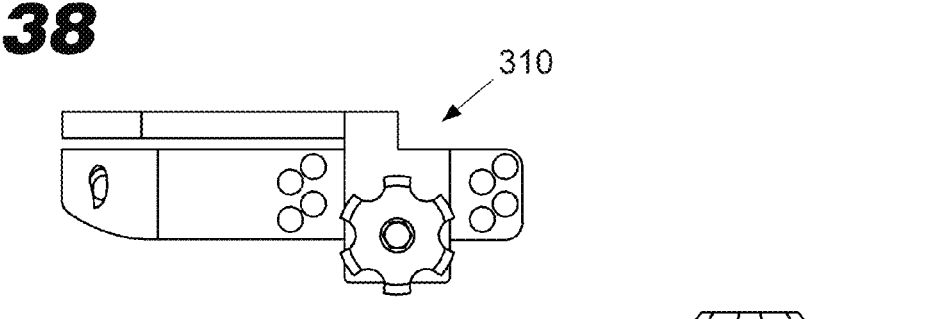
FIG. 38 is a front view of the tibia cutting block assembly shown in FIG. 37.
Figure 39:
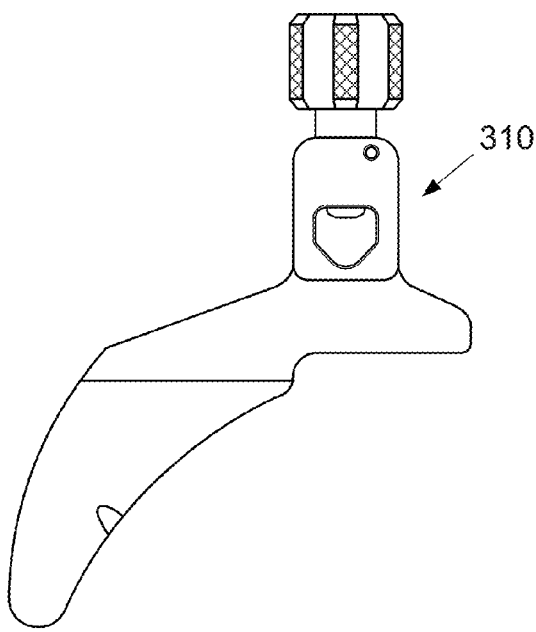
FIG. 39 is a bottom view of the tibia cutting block assembly shown in FIG. 37.

FIGS. 37, 38, and 39 illustrate the tibia cutting block assembly 310. The tibia cutting block assembly 310 includes the tibial cutting block 312 and a knob 314. In some embodiments, the tibia cutting block assembly 310 also includes a spring pin 316 which is used to retain the knob 314 to the cutting block 312. In the depicted embodiments, the tibial cutting block 312 is left-handed, but those of ordinary skill in the art would understand that a right-handed cutting block could also be used.

Figure 40:
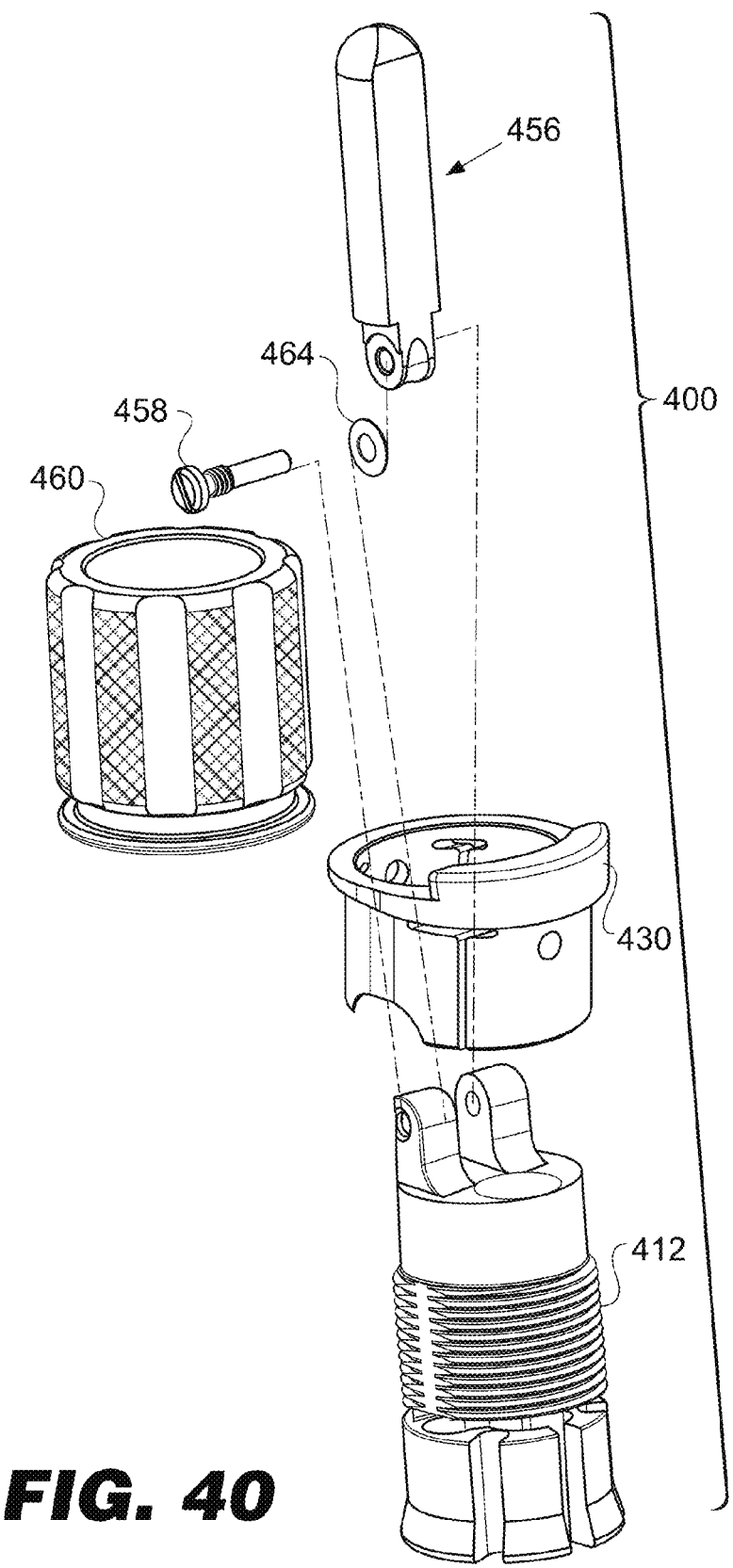
FIG. 40 is an exploded perspective view of the locking instrument assembly in a third embodiment.
Figure 41:
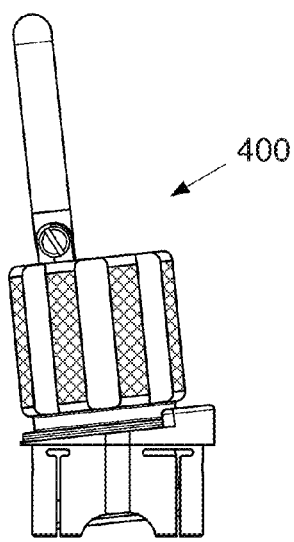
FIG. 41 is a side view of the locking instrument assembly shown in FIG. 40.
Figure 42:
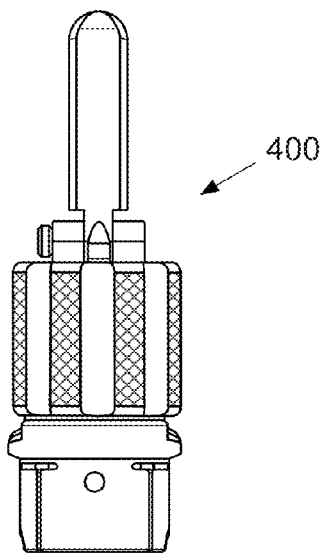
FIG. 42 is a front view of the locking instrument assembly shown in FIG. 40.

FIGS. 40, 41, and 42 illustrate a third embodiment of the locking instrument assembly. The locking instrument assembly 400 includes an inner collet 412, an outer body 430, a handle 456, a fastener 458, a knob 460, and a washer 464. The fastener 458 and the washer 464 are used to mount the handle 456 to the inner collet 412.

Figure 43:
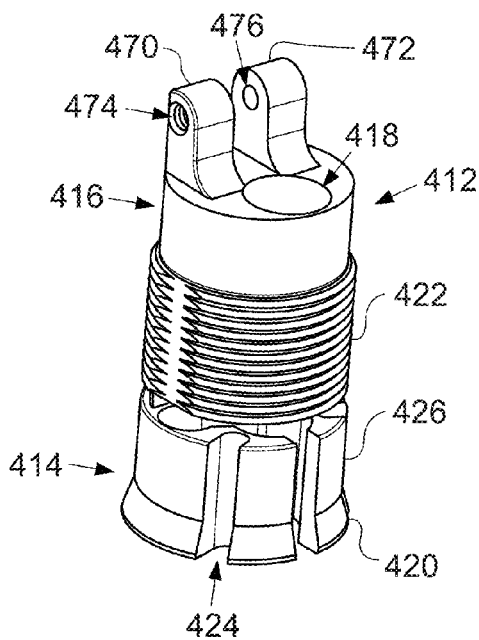
FIG. 43 is a top perspective view of the inner collet in a fourth embodiment.
Figure 44:
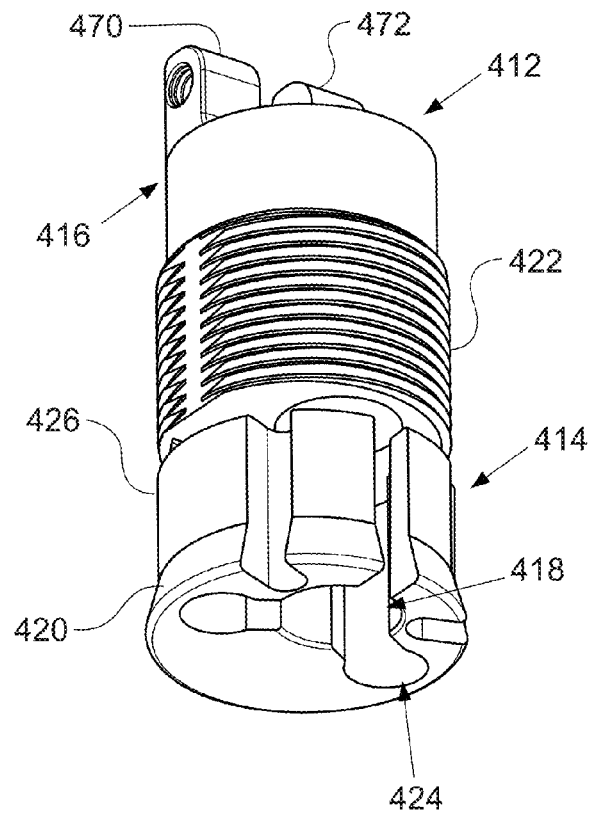
FIG. 44 is a bottom perspective view of the inner collet shown in FIG. 43.

FIGS. 43 and 44 illustrate the inner collet 412. The inner collet 412 has a first end portion 414, a second end portion 416, and a longitudinally extending inner bore 418. The inner bore 418 is adapted to receive the intramedullary device 100. In other words, the inner bore 418 is shaped to fit the intramedullary device 100. The first end portion 414 has a collar 420 and a base portion 426. The base portion 426 may be cylindrical, oval, or cylindrical with tangent portions removed. In the depicted embodiment, the base portion 426 is generally cylindrical. In contrast to the previous embodiments, the inner bore 418 is offset from the central axis of the base portion 426. In other words, the central axis of the inner bore 418 is radially offset a certain distance from the central axis of the base portion 426. This offset distance may be anywhere from about one millimeter to about eighteen millimeters and rather from about two millimeters to about six millimeters. The offset inner bore 418 allows the locking instrument assembly 400 to offset an instrument when the instrument is mounted to the outer body 430.

Inner collet 412 functions as a collet or wedge. The collar 420 may include one or more relief areas 424. The relief areas 424 allow a portion of the inner bore 418 to collapse. In the embodiment depicted in FIG. 44, the collar 420 has five relief areas 424. The relief areas 424 may be cylindrical, rectangular, prolated, or key hole shaped. The second end portion 416 has a fastener member 422. In the embodiment depicted in FIG. 44, the fastener member 422 is a helical groove or thread, but those of ordinary skill in the art would understand that other types of fastening mechanisms may be used.

The inner collet also includes a first projection 470 and a second projection 472. The projections 470, 472 are spaced apart to receive the handle 456 therebetween. The first projection 470 has a first hole 474, and the second projection 472 has a second hole 476. In the embodiments depicted in FIGS. 43 and 44, the first hole 474 and the second hole 476 are coaxial. The first hole 474 and/or the second hole 476 may be threaded. The holes 474, 476 receive the fastener 458, such as a screw, bolt or pin.

Figure 45:
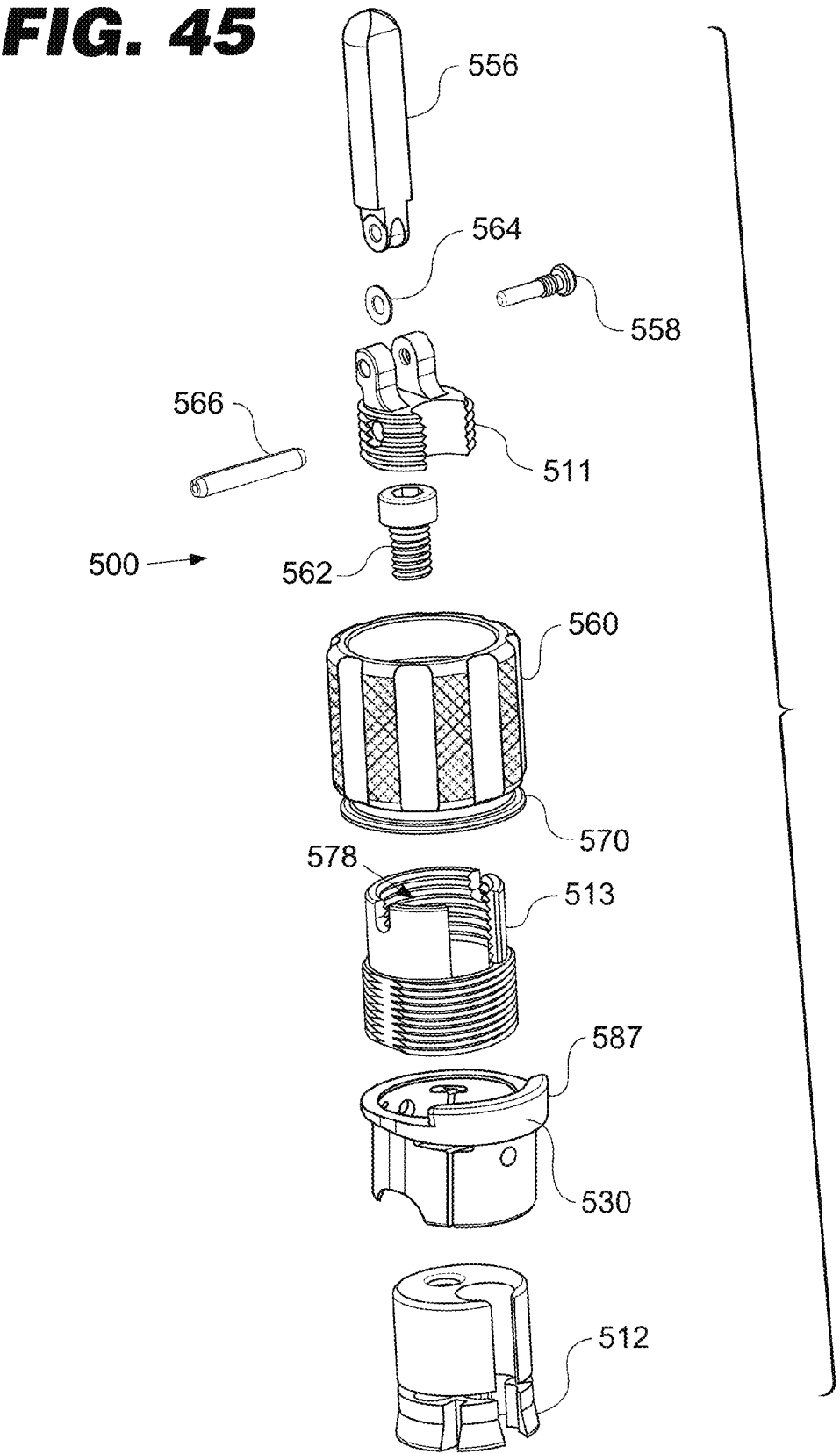
FIG. 45 is an exploded perspective view of the locking instrument assembly in a fourth embodiment.
Figure 46:
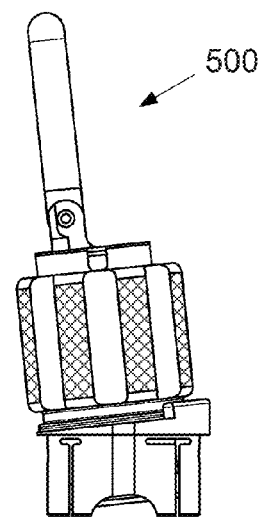
FIG. 46 is a side view of the locking instrument assembly shown in FIG. 45.
Figure 47:
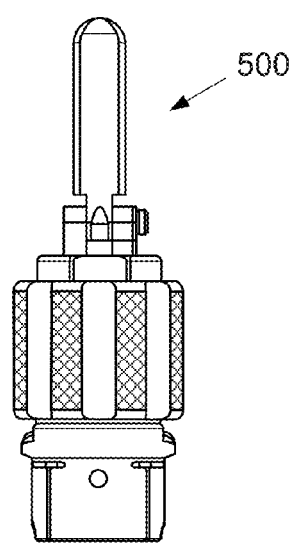
FIG. 47 is a side view of the locking instrument assembly shown in FIG. 45.

FIGS. 45, 46, and 47 illustrate a fourth embodiment of the locking instrument assembly. The fourth embodiment is similar to the third embodiment except the inner collet has at least two portions in the fourth embodiment. The locking instrument 500 includes an inner collet 512, an offset collet handle base 511, an offset collet inner thread 513, an outer body 530, a handle 556, a first fastener 558, a knob 560, a second fastener 562, a washer 564, and a spring pin 566.

The locking instrument assembly 500 is assembled as follows. First, the offset collet inner thread 513 is threaded into the knob 560 until both components are flush at the top. Second, the knob 560 is removably attached to the outer body 530. In the depicted embodiment, the knob 560 has a flange 570 that is received by a recess (not shown) of a shoulder 587 of the outer body 530. Third, the inner collet 512 is inserted through the outer body 530 and into the offset collet inner thread 513. Fourth, the second fastener 562 is installed to secure the inner collet 512 to the offset collet inner thread 513. Fifth, the offset collet handle base 511 is threaded into the offset collet inner thread 513 until both components are nearly flush at the top. Sixth, the knob 560 is tightened. Seventh, the spring pin 566 is inserted through the offset collet inner thread 513 and into the offset collet handle base 511. Eighth, the handle 556 and the washer 564 are placed on the offset collet handle base 511 and the first fastener 558 is inserted into the offset collet handle base 511.

Figure 48:
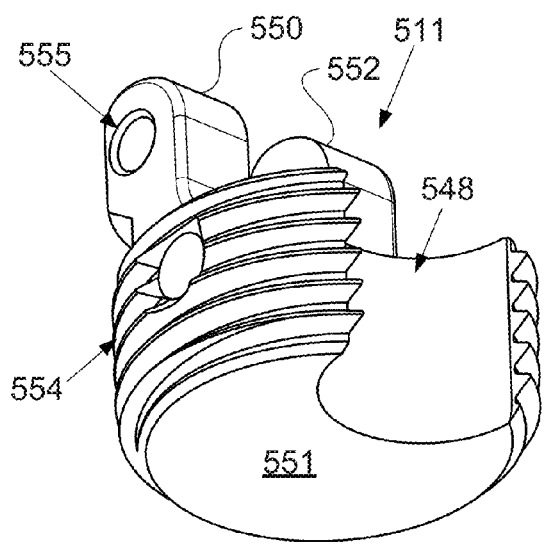
FIG. 48 is a top perspective view of an offset collet handle base.

FIG. 48 illustrates the offset collet handle base 511. The offset collet handle base 511 includes a first projection 550, a second projection 552, a bottom portion 551, and an outer portion 554. The projections 550, 552 are spaced apart to receive the handle 556. The projections 550, 552 each also include a first mounting hole 555. The first mounting holes 555 receive the first fastener 558. The outer portion 554 is adapted to mate with the offset inner thread 513. In the depicted embodiments, the outer portion 554 is threaded, but those of ordinary skill in the art would understand that other methods of engagement may be used. The offset collet handle base 511 also includes the inner bore 548. The inner bore 548 is curved or arcuate. In the embodiment depicted in FIG. 48, the inner bore 548 is in the shape of a semicircle. In some embodiments, the inner bore 548 is substantially circular.

Figure 49:
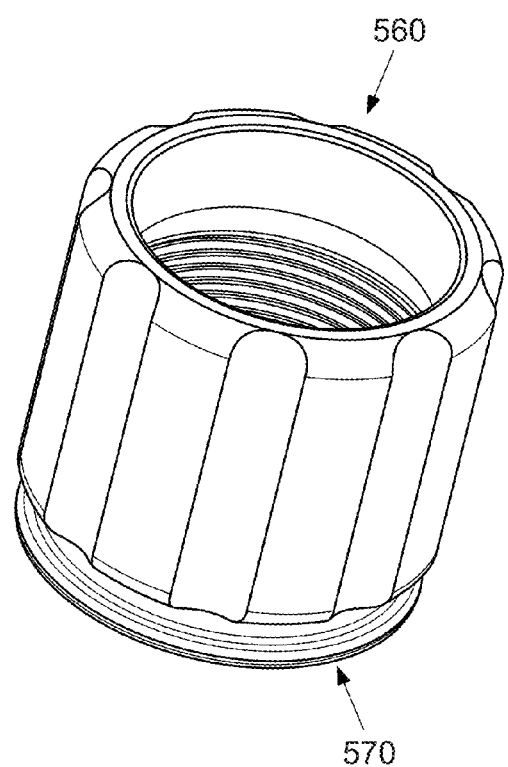
FIG. 49 is a top perspective view of the knob in a fourth embodiment.

FIG. 49 illustrates the knob 560. The knob 560 includes the flange 570.

Figure 50:
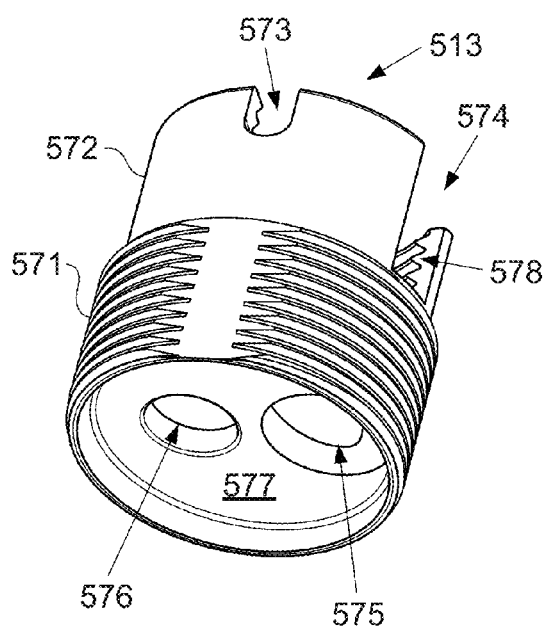
FIG. 50 is a top perspective view of an offset collet inner thread.

FIG. 50 illustrates the offset collet inner thread 513. The offset collet inner thread 513 includes a barrel member 571, a column 572, and a bottom face 577. The barrel member 571 is adapted to mate with the knob 560. In the depicted embodiment, the barrel member 571 is threaded but other methods of engagement may be used. The column 572 extends upwardly from the barrel member 571. The column 572 has cutouts 573 and a vertical slot 574. An inner portion 578 of the column 572 receives the offset collet handle base 511. In the depicted embodiment, the inner portion 578 is threaded but other methods of engagement may be used. The bottom face 577 has an inner bore 575 and a through hole 576. The inner bore 575 is dimensioned and shaped to receive the intramedullary device 100. The through hole 576 is dimensioned and shaped to receive a portion of the second fastener 562. The bottom face 577 engages the inner collet 512.

Figure 51:
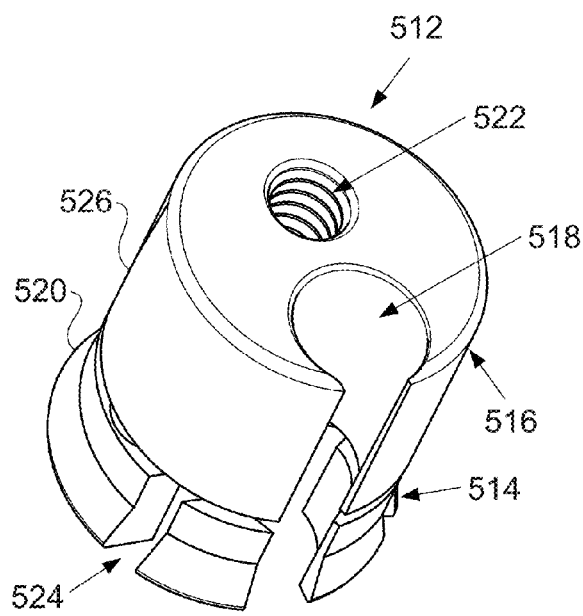
FIG. 51 is a top perspective view of the inner collet in a fourth embodiment.
Figure 52:
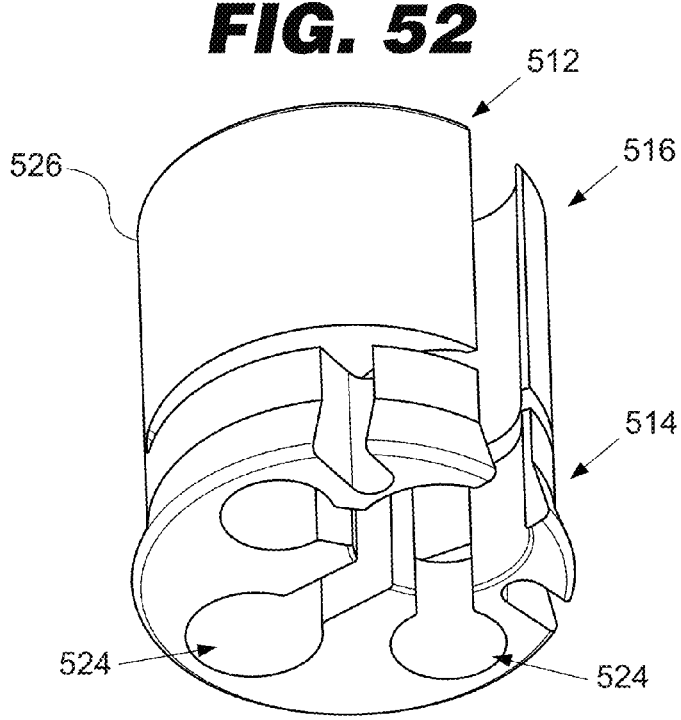
FIG. 52 is a bottom perspective view of the inner collet shown in FIG. 51.

FIGS. 51 and 52 illustrate the inner collet 512. The inner collet 512 has a first end portion 514, a second end portion 516, and a longitudinally extending inner bore 518. The inner bore 518 is curved or arcuate. In the embodiment depicted in FIG. 51, the inner bore 518 is substantially cylindrical. The inner bore 518 is adapted to receive the intramedullary device 100. In other words, the inner bore 518 is shaped to fit the intramedullary device 100. The first end portion 514 has a collar 520 and a base portion 526. The base portion 526 may be cylindrical, oval, or cylindrical with tangent portions removed. In the depicted embodiment, the base portion 526 is generally cylindrical. The inner bore 518 is offset from the central axis of the base portion 526. In other words, the central axis of the inner bore 518 is radially offset a certain distance from the central axis of the base portion 526. This offset distance may be anywhere from about one millimeter to about eighteen millimeters and rather from about two millimeters to about six millimeters. The offset inner bore 518 allows the locking instrument assembly 500 to offset an instrument when the instrument is mounted to the outer body 530.

Inner collet 512 functions as a collet or wedge. The collar 520 may include one or more relief areas 524. The relief areas 524 allow a portion of the inner bore 518 to collapse. In the embodiment depicted in FIG. 52, the collar 520 has five relief areas 524. The relief areas 524 may be cylindrical, rectangular, prolated, or key hole shaped.

The inner collet 512 also includes a second mounting hole 522. The second mounting hole receives a portion of the fastener 562. In the depicted embodiment, the second mounting hole 522 is threaded but other methods of engagement may be used.

The invention also includes a surgical method. Portions of the surgical method utilize the locking instrument assembly. While the depicted embodiments illustrate a surgical method for revision knee arthroplasty, those of ordinary skill in the art would understand that the surgical method and the locking instrument assembly may be used in primary knee arthroplasty. Moreover, while the depicted embodiments illustrate bi-compartmental knee replacement, those of ordinary skill in the art would understand that the surgical method and the locking instrument assembly are equally applicable in uni-compartmental knee replacement.

The surgical method begins with preoperative evaluation. In the case of revision knee arthroplasty, the preoperative evaluation begins with a complete patient history and physical examination. Determination of the etiology or failure may require radiographic evaluation, the use of technetium bone scans, the use of laboratory studies and/or aspiration to rule out the possibility of indolent infection.

The exposure of the total knee may be complicated by previous incisions, stiffness, or a fibrotic soft tissue envelope. In general, greater exposure is required for a revision total knee arthroplasty as compared with that of a primary procedure. Proper tissue planes medially and laterally must be elevated and fasciocutaneous flaps must be maintained in order to minimize wound healing complications. Typically, a standard medial parapatellar arthrotomy is used when feasible. An extensile exposure proximally, such as a quadriceps snip, or distally, such as a tibialtubercle osteotomy, may be required to achieve adequate exposure.

After adequate exposure of all components has been achieved, attention is turned to component removal. This is normally achieved through dissection of the interface between the prosthesis and the cement or at the prosthetic/bone interface. Many surgeons prefer to remove the femoral component first in order to improve visualization of the posterior tibial component. A thin, flexible osteotome or a thin oscillating saw maybe used to disrupt the prosthetic interface in order to allow removal with minimal bone loss. Alternative techniques include the use of a Midas-Rex burr or a Gigli saw to free this interface. Angled osteotomes may be helpful in freeing the condylar portions of the femoral components. If the interfaces have been adequately freed, minimal force is typically required to remove the femoral component. Excessive force to remove the component may lead to femoral fracture.

Removal of the tibial component is then carried out in a similar manner. Occasionally, exposure of the lateral side may be more difficult, and the use of a small capsular incision about the lateral aspect of the joint may be required to gain access to the posterolateral aspect of the tibial component. If disruption of the interface at the level of the plateau does not allow for easy implant removal, a cortical window may be made in the metadiaphysis of the tibia to allow a bone tamp access to the keel of the prosthesis. As bone cement fails most easily in tension, a controlled, well-placed blow will often dislodge the tibial component.

If the patellar button is securely fixed, well-positioned and does not show excessive wear then it may be left and protected for the remainder of the case. If the patellar button must be revised, removal is most easily performed with a sagittal saw at the cement interface. Remaining cement and polyethylene plugs from the component may then be removed with a small, high-speed burr. Great care must be taken during this stage of the procedure in order to ensure adequate patellar bone stock remains for revision component placement so that fracture is prevented. Once components have been removed, the remaining cement can then be removed with curettes, rongeurs or cement osteotomes. The wounds may be irrigated with a water pick to remove loose debris and attention can then be turned to the reconstructive portion of the surgical method.

Figure 53:
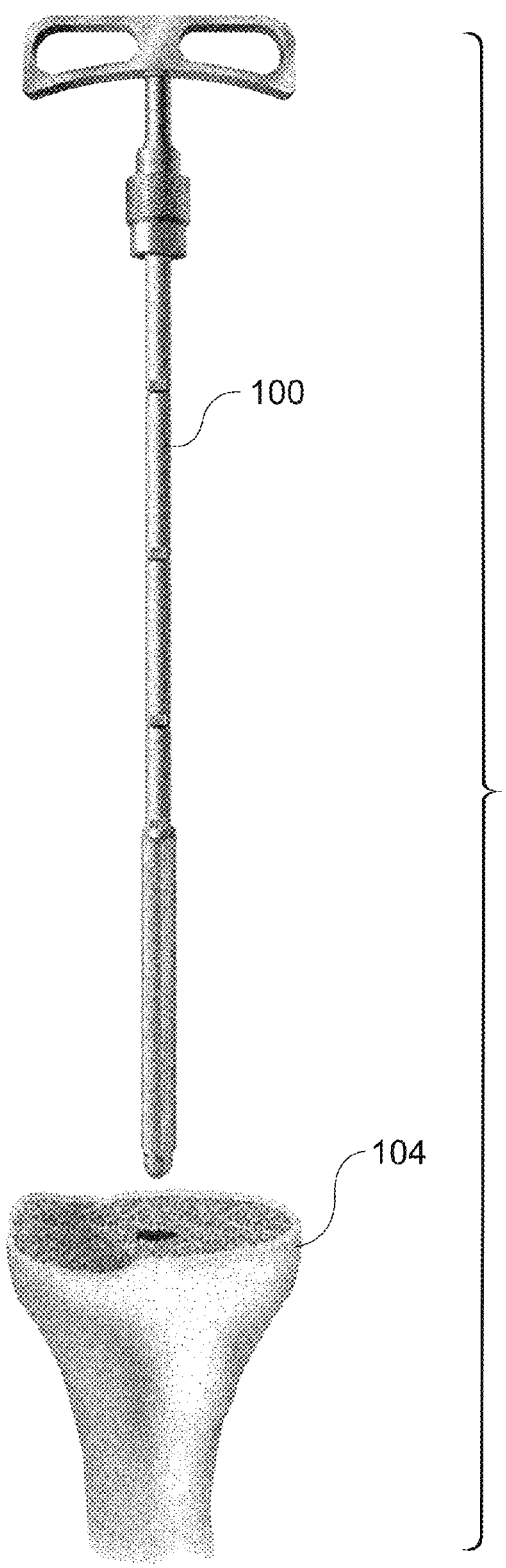
FIG. 53 is a front view of an intramedullary device and a tibia.

FIG. 53 is a front view of an intramedullary device 100 and a tibia 104. In an optional first step, a pilot hole may be drilled into the tibia 104 using an intramedullary drill. The intramedullary canal is reamed until cortical contact is achieved using progressively larger diameter reamers. The intramedullary device 100 is placed or left in the reamed intramedullary canal. The intramedullary device 100 may be the last reamer used to ream the canal or it may be a trial stem connection rod assembly. In the case of the trial stem connection rod assembly, a note is made as to the depth and diameter of the last reamer, the appropriate diameter trial stem connection rod is selected, and the trial stem connection rod assembly is inserted into the tibial canal. For this purpose, the reamers may include depth indicators.

Figure 54:
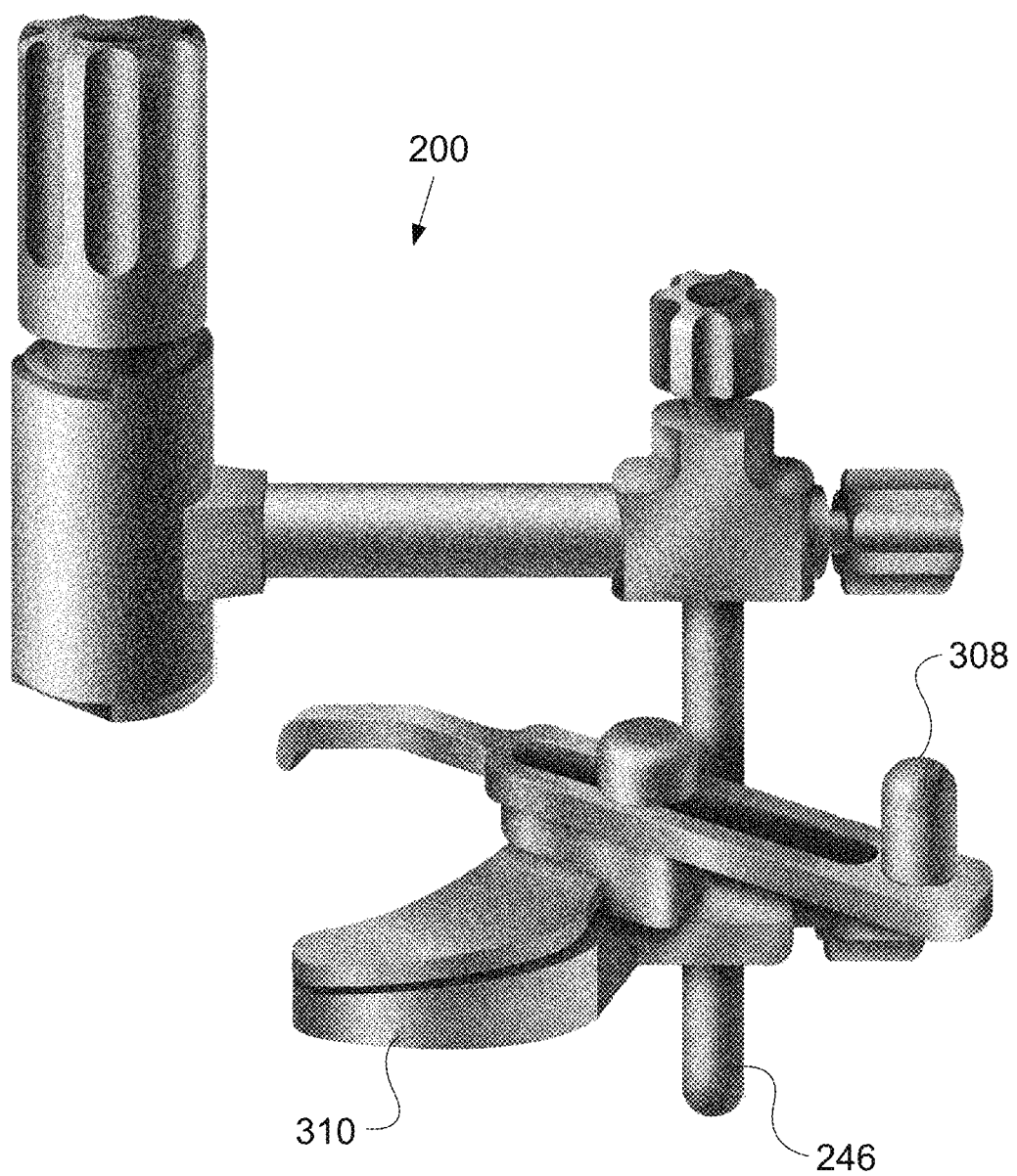
FIG. 54 is a side perspective view of the locking instrument assembly.
Figure 55:
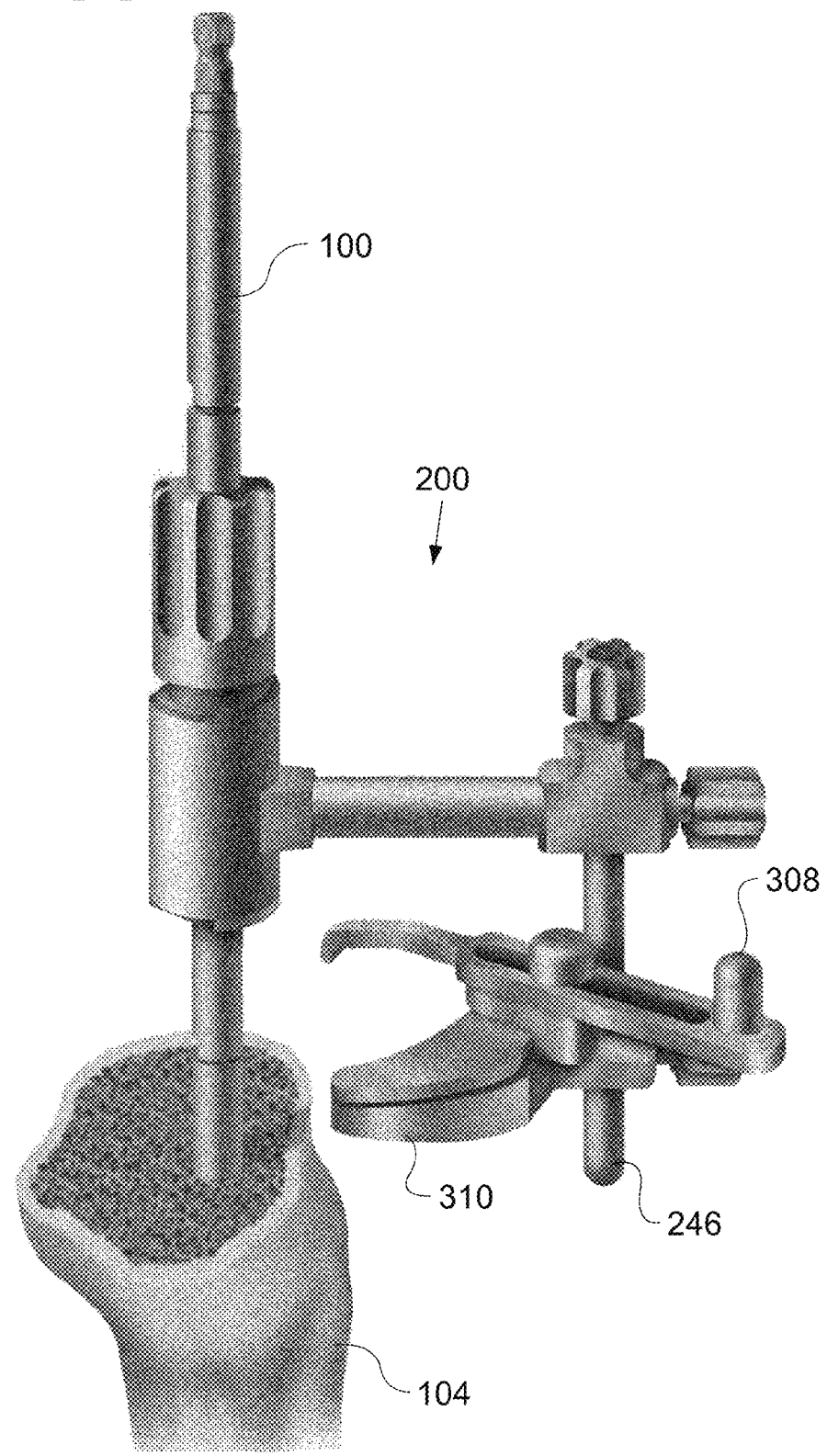
FIG. 55 is a front perspective view of the locking instrument assembly as mounted on the intramedullary device.

Next, the tibial alignment guide is assembled to the locking instrument assembly, and the locking instrument assembly is mounted to the intramedullary device 100. Referring now to FIG. 54, a stylus 308 is connected to the tibial cutting block 310. Then, the tibial cutting block 310 is assembled to the down rod 246. Next, as best seen in FIG. 55, the locking instrument assembly 200 is slid onto the intramedullary device 100. The down rod 246 is adjusted towards the anterior tibia and locked into position. The locking instrument assembly 200 is lowered until the stylus 308 touches the least affected area of the tibial plateau. The knob 60, 90, 260 is tightened to lock the locking instrument assembly in place. Thereafter, the tibial cutting block 310 may be rotated around the anterior tibia for optimum access by loosening the rotation lock knob 242.

Figure 57:
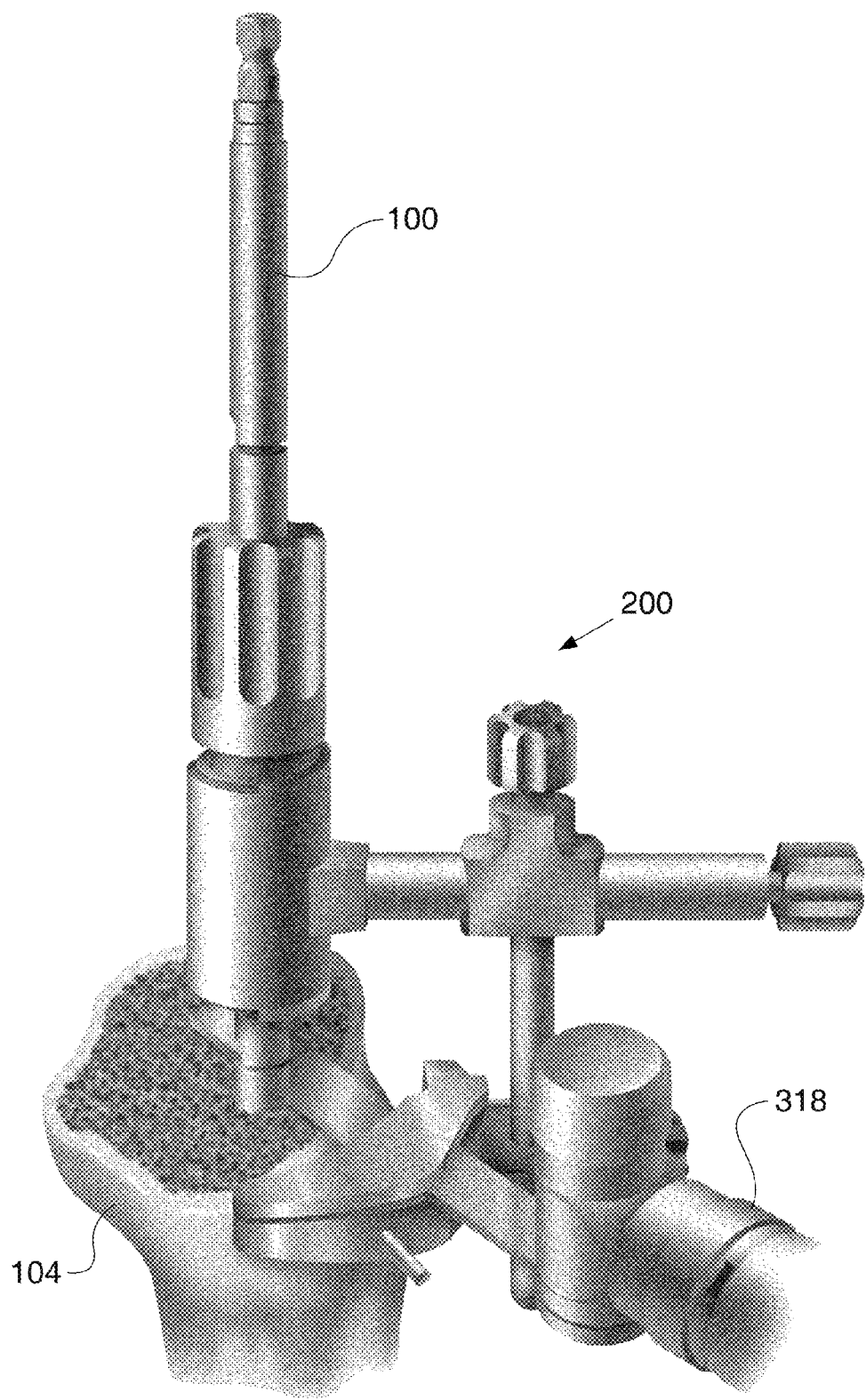
FIG. 57 is a front perspective view of the locking instrument assembly as utilized in a resection.

Referring to FIGS. 56 and 57, the next step is resection of the tibia. An optional first step is to use a fastener driver, such as a hex screwdriver, to tighten the rotational lock knob, translation lock knob, and the cutting block lock knob. A second optional step is to pin the tibial cutting block to the tibia. Pins 313 may be used to pin the cutting block 310. The stylus 308 is removed, a saw blade is inserted into the tibial cutting block, and the tibia is resected. The locking instrument assembly is removed. Thereafter, the surgeon may perform typical steps for tibial preparation. This may include the steps of counterboring the tibia, inserting a trial into the tibia, assessing the tibial trial, and adjusting the tibia for proper trial alignment.

The surgical method also includes step for femoral preparation to receive an implant. FIG. 58 illustrates an intramedullary device 100 and a femur 102. In an optional first step, a pilot hole may be drilled into the femur 102 using an intramedullary drill. The intramedullary canal is reamed until cortical contact is achieved using progressively larger diameter reamers. The intramedullary device 100 is placed or left in the reamed intramedullary canal. The intramedullary device 100 may be the last reamer used to ream the canal or it may be a trial stem connection rod assembly. In the case of the trial stem connection rod assembly, a note is made as to the depth and diameter of the last reamer, the appropriate diameter trial stem connection rod is selected, and the trial stem connection rod assembly is inserted into the femoral canal. For this purpose, the reamers may include depth indicators.

Figure 59:
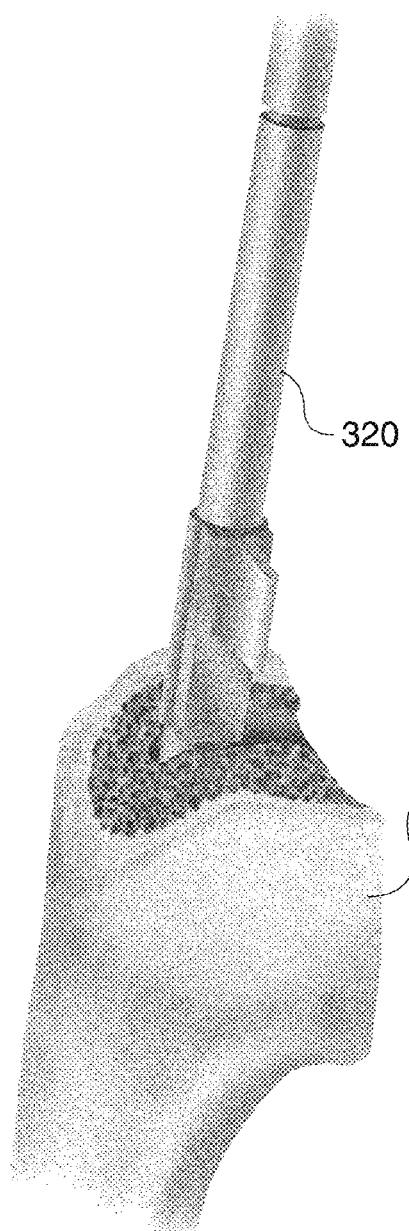
FIG. 59 is a front perspective view of an offset indicator.
Figure 60:
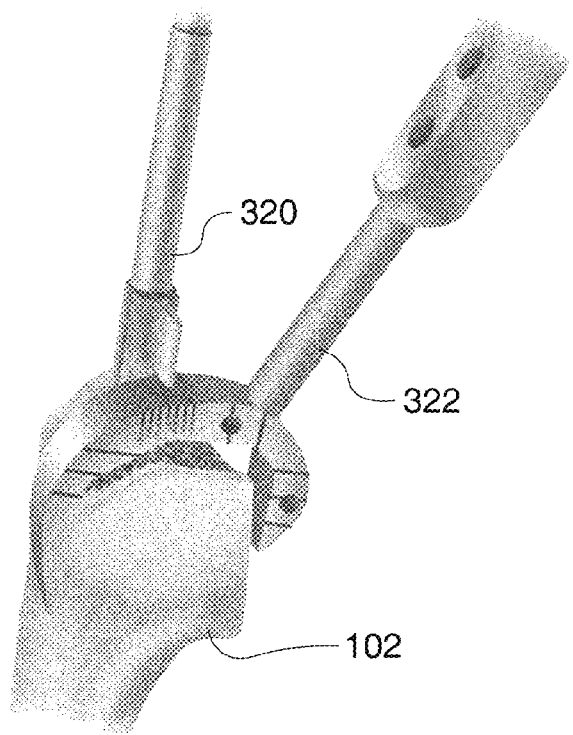
FIG. 60 is a side perspective view of the offset indicator and an anterior-posterior sizing plate.

Next, the femur 102 is assessed for anterior-posterior size and stem offset position. As best seen in FIGS. 59 and 60, an offset indicator 320 is slid over the intramedullary device 100 and an anterior-posterior sizing plate 322 is positioned relative to the anterior cortex of the femur and adjacent to the offset indicator. The anterior-posterior size is assessed. Once the anterior-posterior size is determined, the offset indicator is used to assess the anterior-posterior position relative to the reamer position. The offset indicator 320 is rotated parallel to the epicondylar axis and a note is made of the offset indicator stylus position relative to the offset markings on the medial face of the anterior-posterior sizing plate. Thereafter, the offset indicator 320 and the anterior-posterior sizing plate 322 are removed.

Figure 61:
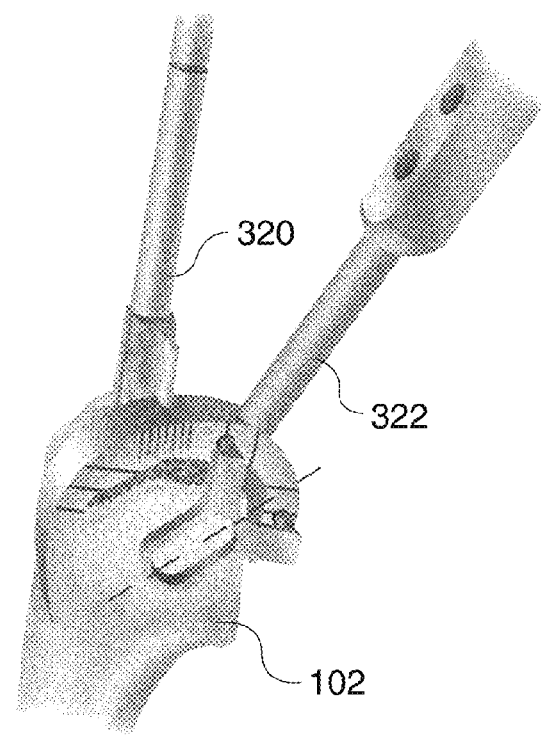
FIG. 61 is a side perspective view of the offset indicator, the anterior-posterior sizing plate, and an epicondylar axis target.

Alternatively, the surgeon may assess the offset using the epicondyles. FIG. 61 illustrates an epicondylar axis target 324. After the offset indicator and anterior-posterior sizing plate are installed, the surgeon aligns the center of the epicondyles along the line markings of the epicondylar axis target. It is not necessary to have the center of the epicondyles within the open space of the target axis. The surgeon varies the anterior-posterior sizing plate and distal augment estimates until the epicondyles align with the epicondylar axis target. The goal is to restore the desired joint line positioning. Once a desired position of the anterior-posterior sizing plate is achieved relative to the femoral epicondyles, the surgeon assesses the distal and posterior wedge by referencing the wedge resection level marks on the anterior-posterior sizing plate. The surgeon retains position of the anterior-posterior sizing plate and notes the offset indicator position relative to the indicator marking on the medial face of the anterior-posterior sizing plate. This provides a rough estimate of the offset needed.

Figure 62:
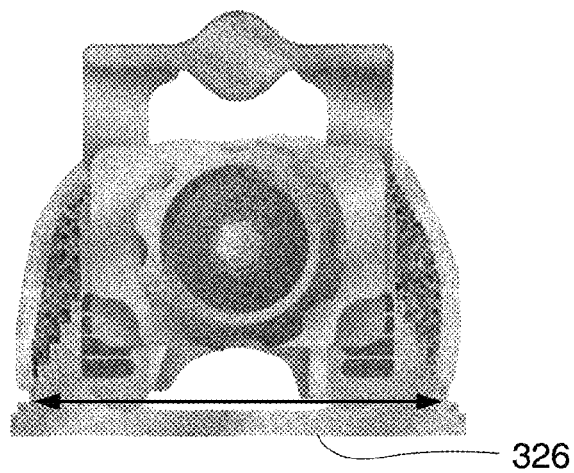
FIG. 62 is a front view of a valgus guide sizing plate.
Figure 63:
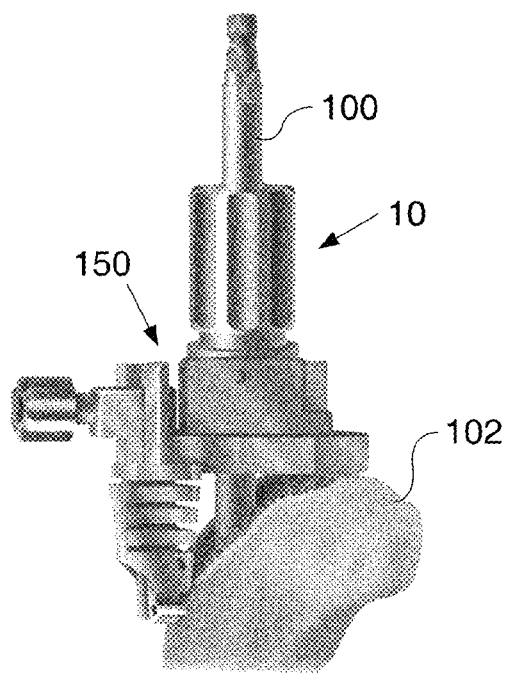
FIG. 63 is a side view of the locking instrument assembly as mounted on the intramedullary device.
Figure 64:
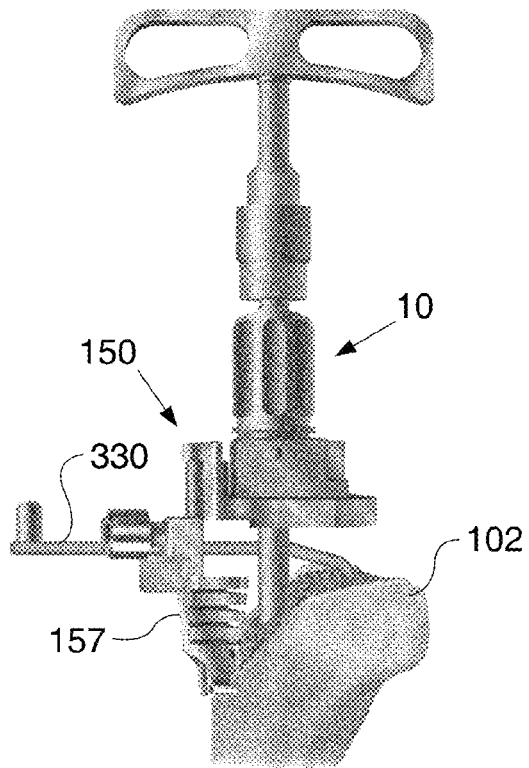
FIG. 64 is a side view of the locking instrument assembly as mounted on the intramedullary device.
Figure 65:
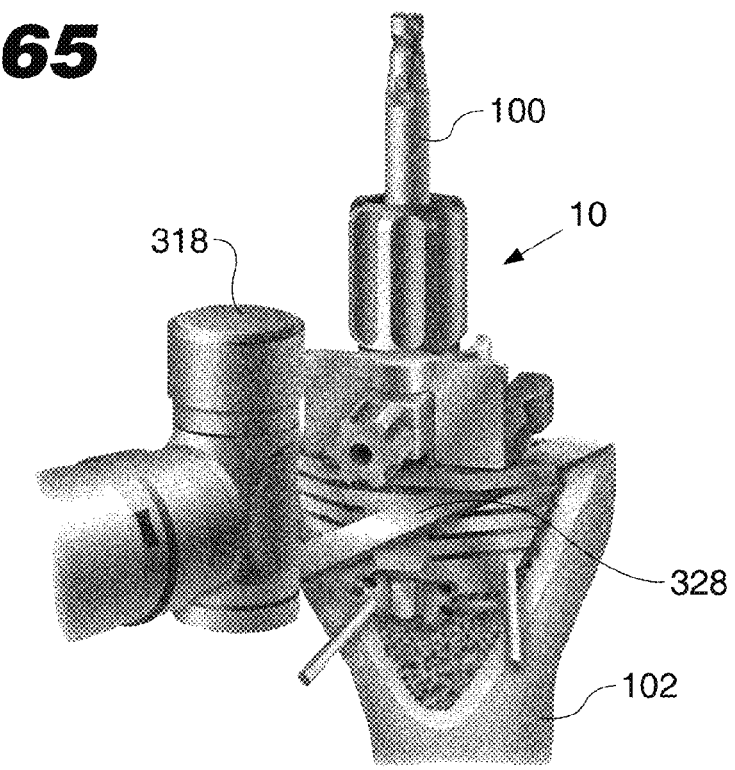
FIG. 65 is a top perspective view of the locking instrument assembly as utilized in a femoral resection.
Figure 66:
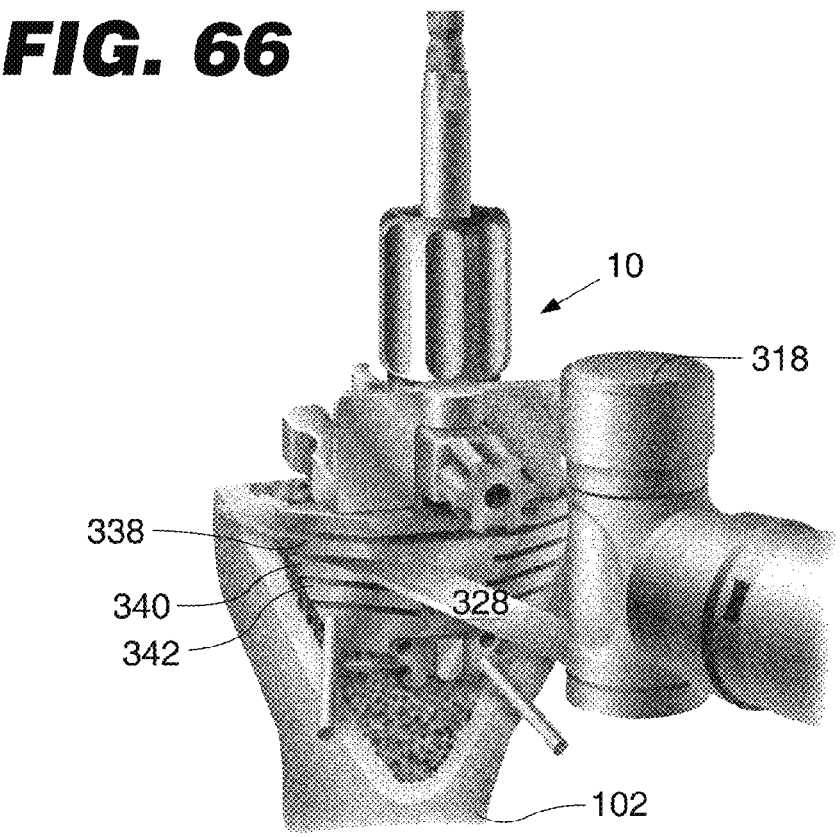
FIG. 66 is a top perspective view of the locking instrument assembly as utilized in a femoral resection.
Figure 67:
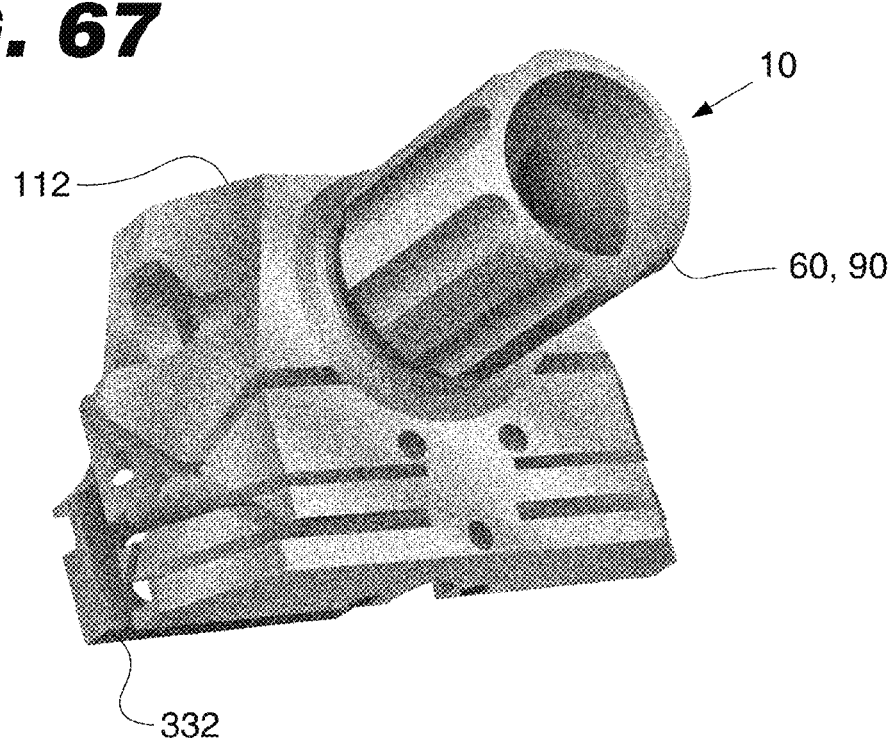
FIG. 67 is a front perspective view of a cutting block mounted on the locking instrument assembly.
Figure 68:
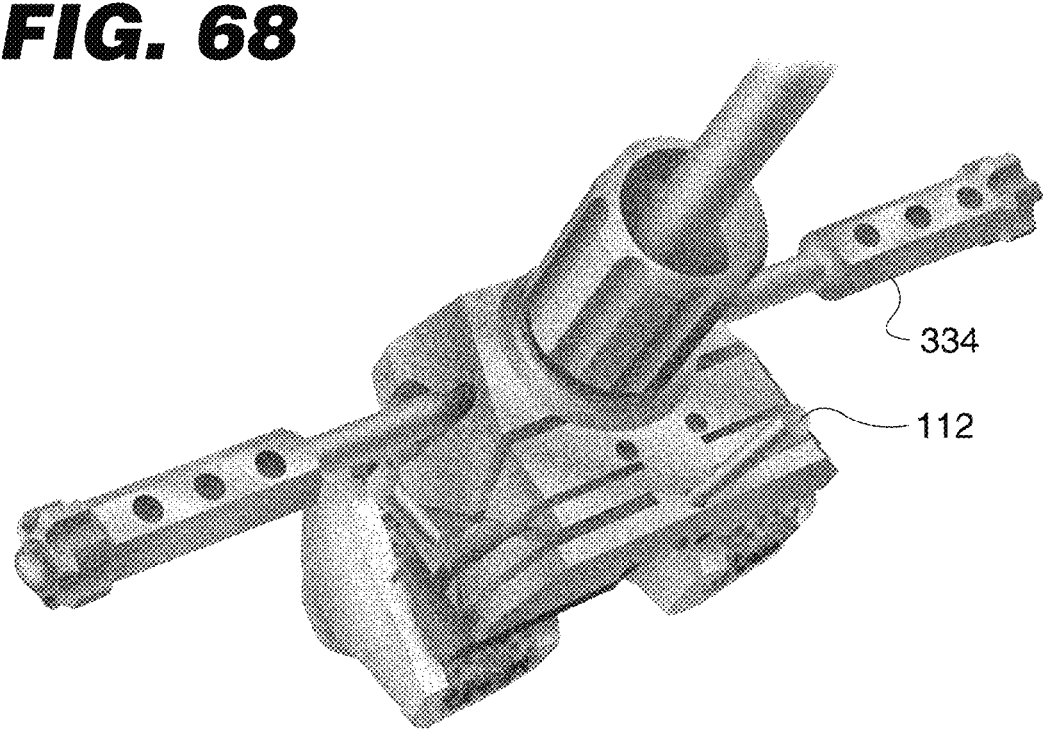
FIG. 68 is a front perspective view of quick connect handles connected to the cutting block.
Figure 69:
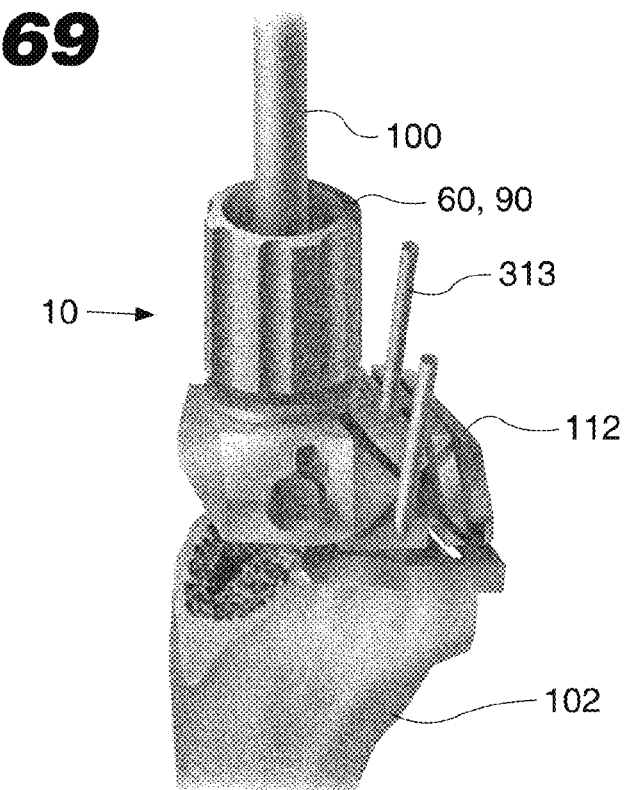
FIG. 69 is a side perspective view of the cutting block and the neutral locking instrument assembly.
Figure 70:
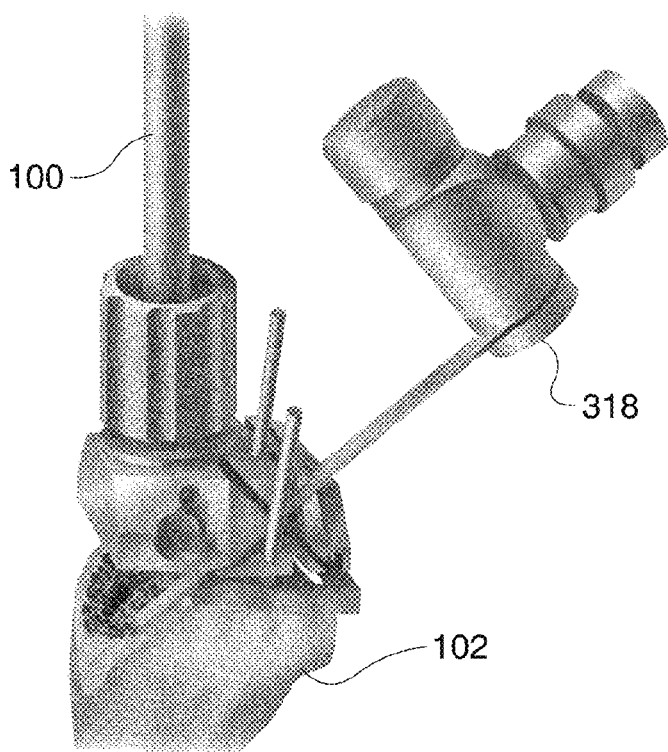
FIG. 70 is a side perspective view of the locking instrument assembly as utilized in a femoral resection.
Figure 71:
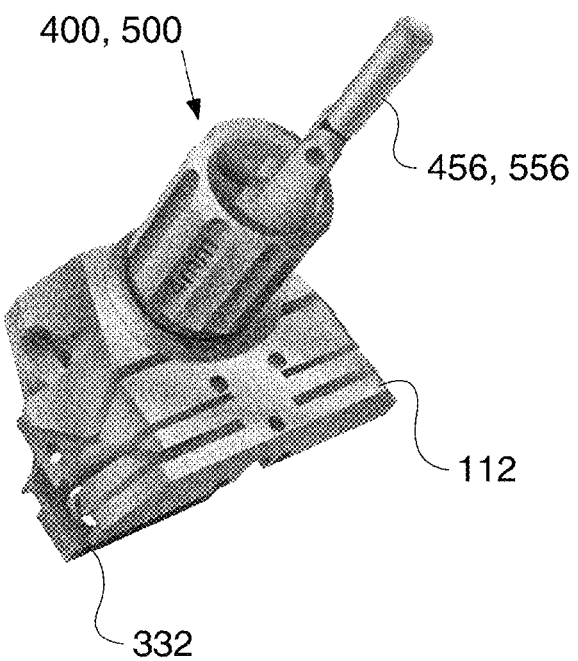
FIG. 71 is a top perspective view of an offset cutting block mounted on the locking instrument assembly.
Figure 72:
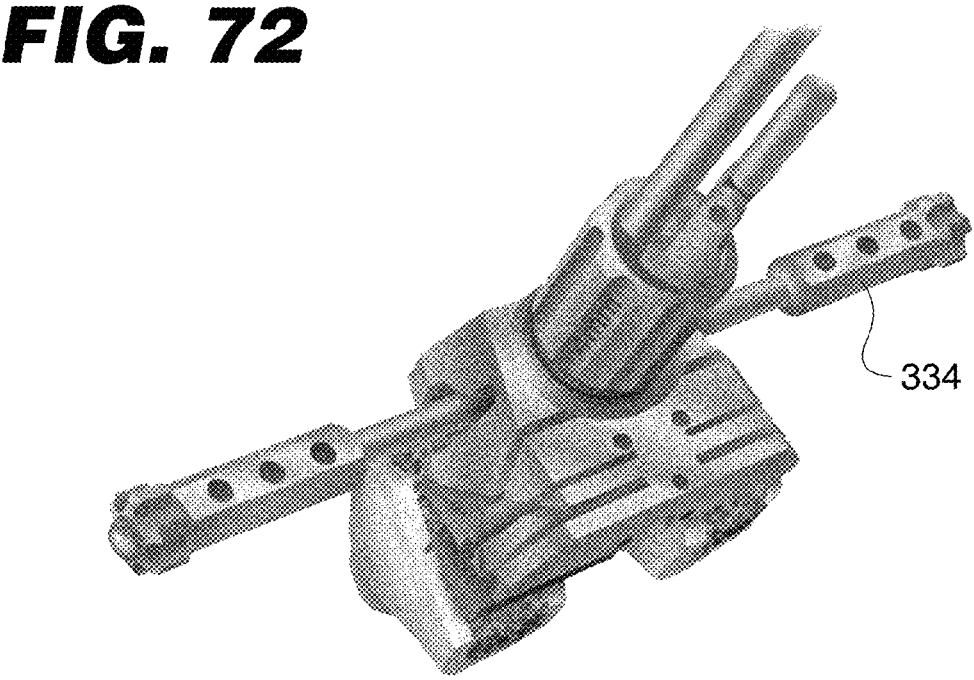
FIG. 72 is a front perspective view of quick connect handles connected to the cutting block.

In an optional step, the surgeon may assess the medial-lateral femoral sizing. A valgus alignment guide is attached to the locking instrument assembly, and the locking instrument assembly is attached to the intramedullary device. A distal cutting block is attached to the valgus alignment guide. As best seen in FIG. 62, a valgus guide sizing plate 326 is attached to the valgus alignment guide. Thereafter, the surgeon assesses the medial-lateral femoral size with the size correlating steps of the valgus guide sizing plate in relation to the femur 102.

Referring now to FIGS. 63 through 66, the next step is resection of the femur. The valgus guide assembly 150 is attached to the locking instrument assembly 10, and the locking instrument assembly 10 is attached to the intramedullary device 100. The locking instrument assembly 10 is slid down the intramedullary device 100 until the valgus guide assembly 150 is flush with the distal femur. Alternatively, a stylus 330 is attached to the distal cutting block 157, and a tip of the stylus 330 is positioned on the least affected side. An optional first step is to use a fastener driver, such as a hex screwdriver, to tighten the valgus collet. A second optional step is to pin the distal cutting block 157 to the femur 102. The stylus 330 is removed, a saw blade 328 is inserted into the distal cutting block 157, and the femur is resected. In some embodiments of the method, it may be necessary to resect an additional femoral wedge. The saw blade 328 is inserted into the second or third slot and the femur is resected. Thereafter, any pins 313 are removed and the valgus guide assembly 150 is removed.

The femoral implant may be neutral or offset from the intramedullary canal. Typically, a neutral placement is selected unless this will result in poor bone by the implant. In that case, an offset placement must be selected.

FIGS. 67 to 70 illustrate a neutral resection of the distal femur. An anterior-posterior hemi distal shim 332 is attached to the anterior-posterior cutting block 112, and the locking instrument assembly 10 is attached to the anterior-posterior cutting block 112. The locking instrument assembly 10 is slid over the intramedullary device 100 until the shim contacts the femur 102. In some embodiments, quick connect handles 334 are connected to the anterior-posterior cutting block 157. The anterior-posterior position and the medial-lateral position of the anterior-posterior cutting block 112 is checked to ensure the anterior-posterior cutting block 112 is properly located with respect to the epicondylar axis. If the anterior-posterior cutting block 112 is not in the appropriate position, an offset resection and placement may be required. The knob 60, 90 is tightened. Optionally, the anterior-posterior cutting block 112 may be pinned to the femur 10 using pins 313. The femur 102 is then resected using saw 318. Thereafter, the surgeon may perform typical steps for femoral preparation. This may include the steps of counterboring the femur, inserting a trial into the femur, assessing the femoral trial, and adjusting the femur for proper trial alignment.

Figure 73:
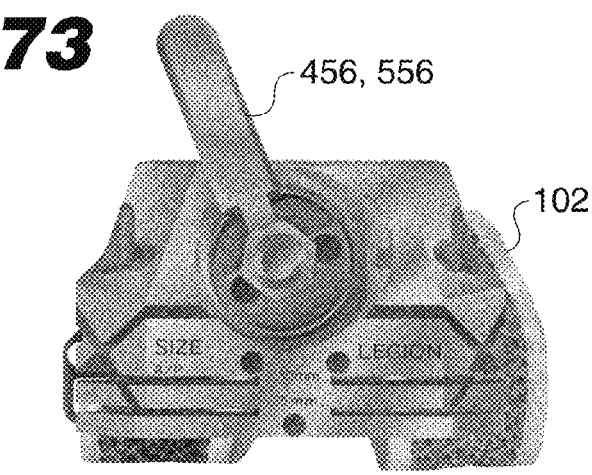
FIG. 73 is a front view of the offset femoral cutting block in a first orientation.
Figure 74:
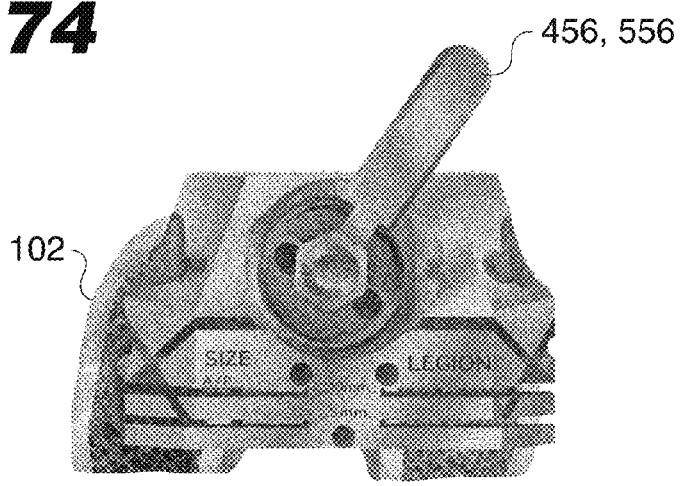
FIG. 74 is a front view of the offset femoral cutting block in a second orientation.
Figure 75:
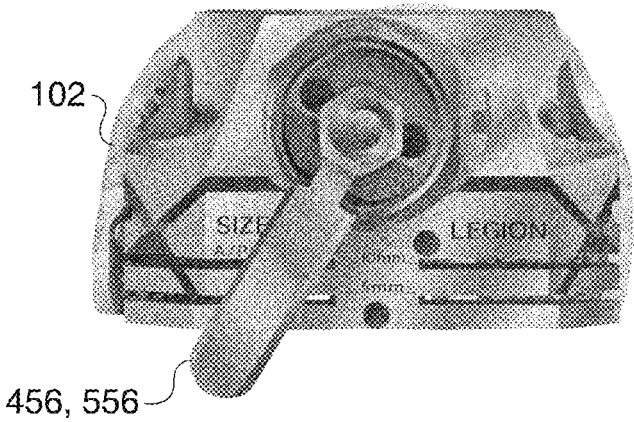
FIG. 75 is a front view of the offset femoral cutting block in a third orientation.
Figure 76:
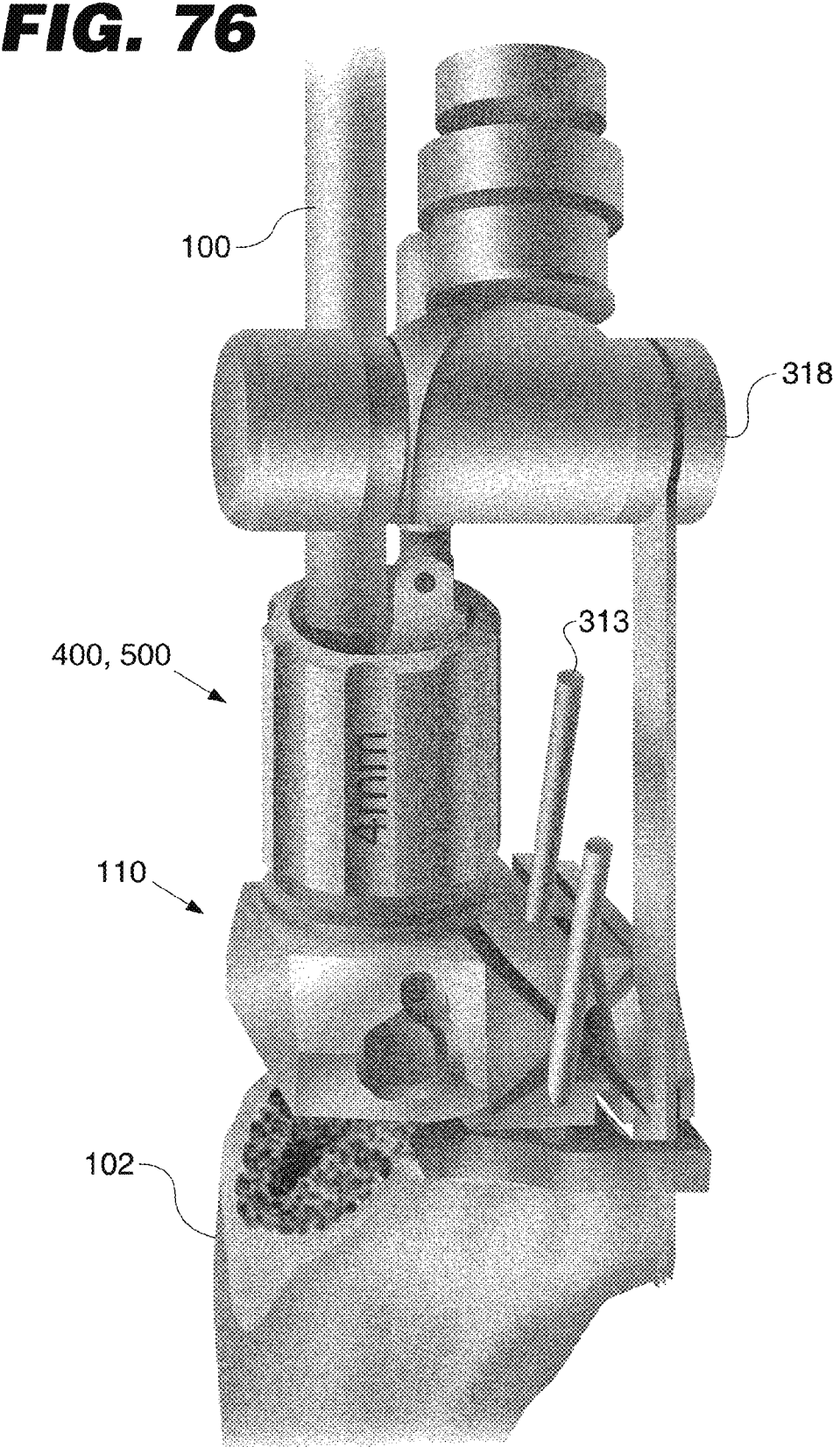
FIG. 76 is a side perspective view of the offset locking instrument assembly.
Figure 77:
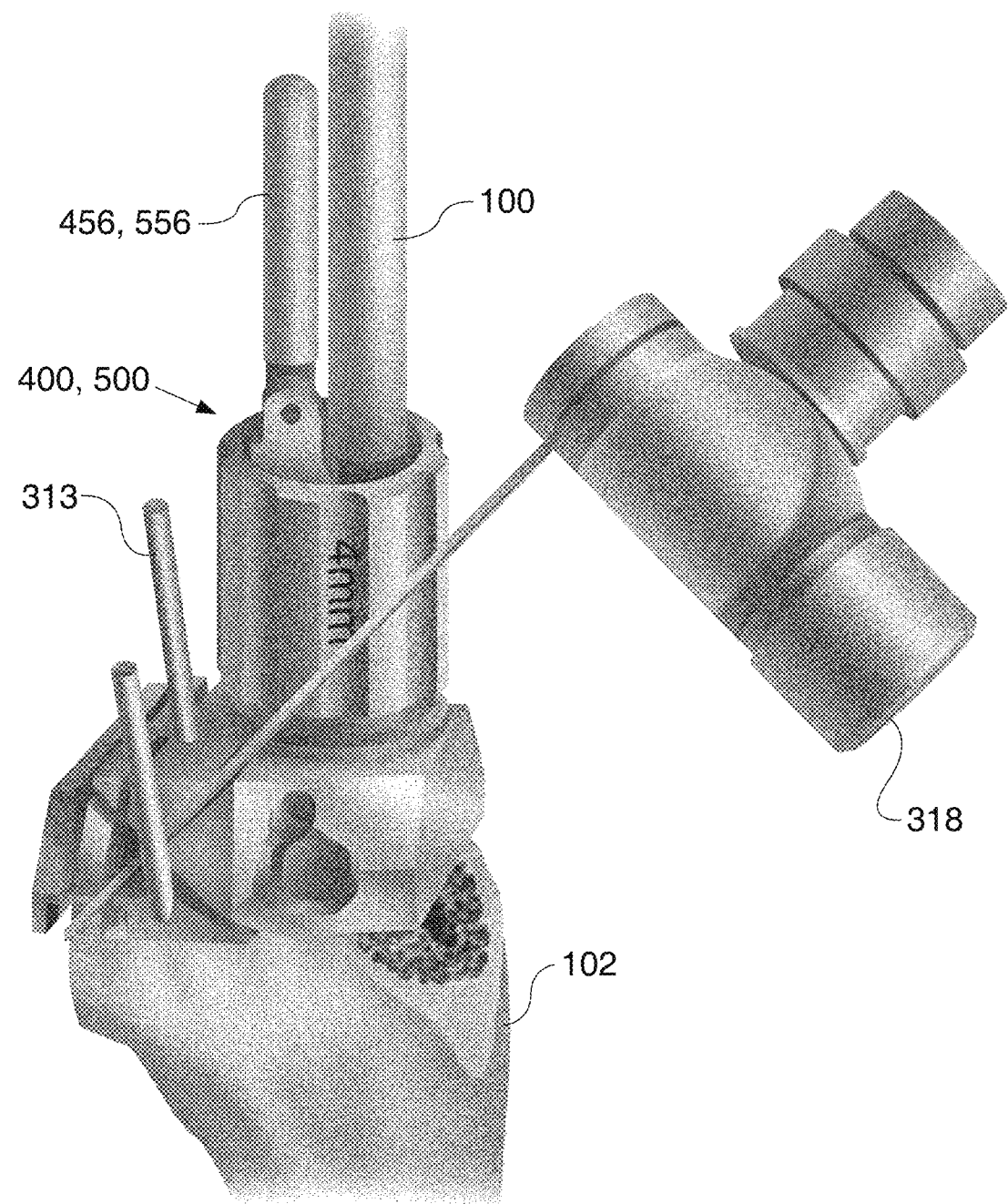
FIG. 77 is a side perspective view of the offset locking instrument assembly.

FIGS. 71 through 77 illustrate an offset resection of the distal femur. The anterior-posterior hemi distal shim 332 is attached to the anterior-posterior cutting block 112, and the offset locking instrument assembly 400, 500 is attached to the anterior-posterior cutting block 112. The locking instrument assembly 400, 500 is slid over the intramedullary device 100 until the shim contacts the femur 102. In some embodiments, quick connect handles 334 are connected to the anterior-posterior cutting block 157. The handle 456, 556 is rotated until the anterior-posterior cutting block 112 is appropriately positioned. The clock position of the handle 456, 556 references or indicates the positioning of the anterior-posterior cutting block relative to the intramedullary canal. FIG. 73 illustrates an "11 O'clock" position. FIG. 74 illustrates a "1 O'clock" position. FIG. 75 illustrates a "7 O'clock" position. When the anterior-posterior cutting block is appropriately positioned, the knob 460, 560 is tightened. Optionally, the anterior-posterior cutting block 112 may be pinned to the femur 10 using pins 313. The femur 102 is then resected using saw 318. Thereafter, the surgeon may perform typical steps for femoral preparation. This may include the steps of counterboring the femur, inserting a trial into the femur, assessing the femoral trial, and adjusting the femur for proper trial alignment.

The instrument and method have several advantages over the state of the art. Most instruments use bone spikes or pins to locate and mount the instrument. Some instruments use an intramedullary device as a reference axis but do not use the intramedullary device to control movement. Still others utilize an intramedullary device that has a pre-set length configuration. In other words, the instrument cannot be adjusted axially along the intramedullary device for a particular patient.

Figure 14:
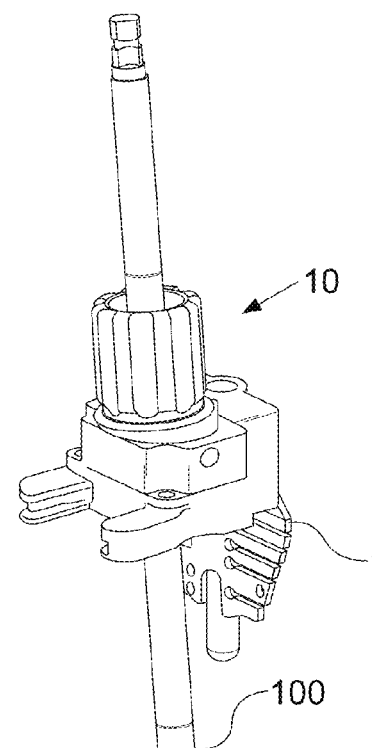
FIG. 14 is a front perspective view of a second instrument attached to the locking instrument assembly.
Figure 15:
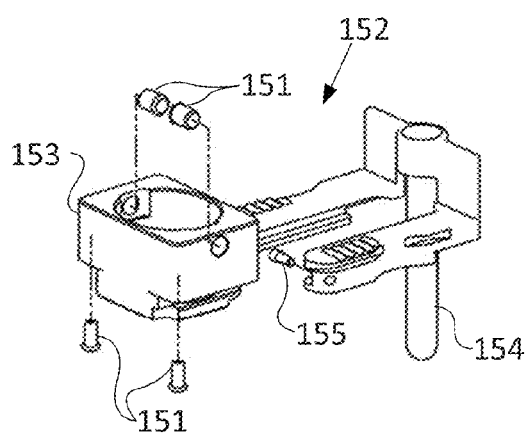
FIG. 15 is an exploded perspective view of a first portion of the second instrument shown in FIG. 14.
Figure 16:
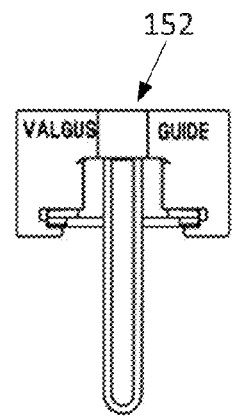
FIG. 16 is a rear view of the first portion shown in FIG. 15.
Figure 17:
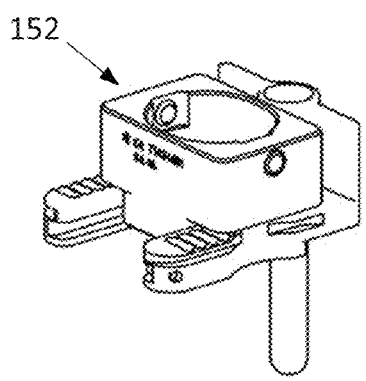
FIG. 17 is a front perspective view of the first portion shown in FIG. 15.
Figure 18:
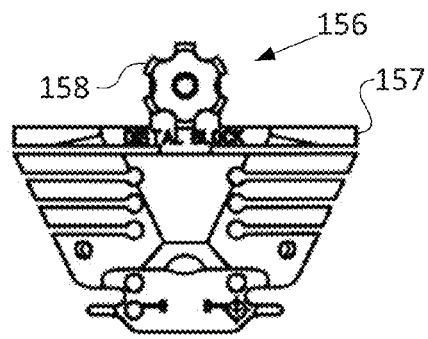
FIG. 18 is a top view of a second portion of the second instrument shown in FIG. 14.
Figure 19:
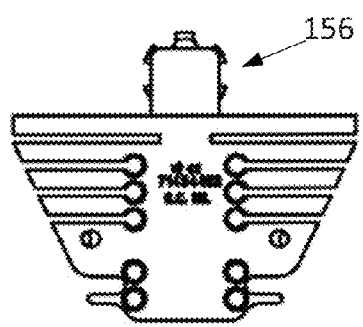
FIG. 19 is a bottom view of the second portion shown in FIG. 18.
Figure 20:
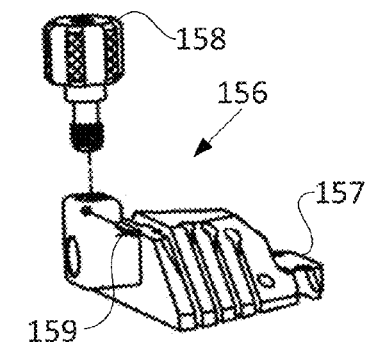
FIG. 20 is an exploded perspective view of the second portion shown in FIG. 18.

The locking instrument assembly 10 allows for instrument adjustment axially along the intramedullary device 100. By not restricting the usable length portion of the intramedullary device, a surgeon can first stabilize the intramedullary device 100 independently from the correlating/desired connecting instrument and then rigidly connect the correlating instrument to the locking instrument assembly 10. For example, FIG. 2 illustrates the locking instrument assembly 10 and the intramedullary device 100. In the embodiment depicted in FIG. 10, an anterior-posterior cutting block 110 is operatively connected to the outer body 30. In another example, FIG. 14 illustrates the locking instrument assembly 10 and the intramedullary device 100. In the embodiment depicted in FIG. 14, a valgus alignment guide 150 is operatively connected to the outer body 30.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for positioning an instrument relative to an intramedullary device, comprising:
   placing the intramedullary device in a bone;
   sliding an instrument assembly over the intramedullary device after placing the intramedullary device in the bone, the instrument assembly including an inner collet, a locking member, and a knob;
   adjusting an angle of a cutting guide associated with the instrument assembly such that the cutting guide is off-axis relative to a longitudinal axis of the intramedullary device;
   tightening the knob such that the locking member causes the inner collet to apply a clamping force to the intramedullary device; and
   making a planar cut that is guided by a surface of the cutting guide.

2. The method of claim 1 wherein adjusting an angle of the cutting guide comprises adjusting a valgus angle of the cutting guide.

3. The method of claim 2 wherein adjusting the valgus angle of the cutting guide comprises engaging the knob with an angled portion of the locking member.

4. The method of claim 1, wherein sliding the instrument assembly over the intramedullary device comprises sliding the instrument assembly such that the intramedullary device extends through the knob.

5. The method of claim 1, wherein sliding the instrument assembly over the intramedullary device comprises sliding, over the intramedullary device, an instrument assembly in which the knob is configured to rotate relative to the inner collet.

6. The method of claim 1, wherein sliding the instrument assembly over the intramedullary device comprises sliding, over the intramedullary device, an instrument assembly in which the inner collet and the knob define a common, central longitudinal axis and the intermediate body locking member defines a central longitudinal axis that is angularly offset relative to the common axis.

7. A method for positioning an instrument relative to an intramedullary device, comprising:
   sliding an instrument assembly over the intramedullary device, the instrument assembly including an inner collet, a locking member, and a knob, wherein sliding the instrument assembly over the intramedullary device comprises sliding the instrument assembly such that the intramedullary device extends through the knob;
   adjusting an angle of a cutting guide associated with the instrument assembly such that the cutting guide is off-axis relative to a longitudinal axis of the intramedullary device;
   tightening the knob such that the locking member causes the inner collet to apply a clamping force to the intramedullary device; and
   making a planar cut that is guided by a surface of the cutting guide.

8. The method of claim 7 wherein adjusting the angle comprises providing the locking member with an outside diameter angled relative to an inside diameter of the locking member.

9. The method of claim 7, wherein tightening the knob comprises rotating the knob about the intramedullary device.

10. The method of claim 7, further comprising implanting an implant at a bone surface formed by the planar cut.

11. The method of claim 7, wherein adjusting an angle of the cutting guide comprises adjusting a valgus angle of the cutting guide.

12. A method for positioning an instrument relative to an intramedullary device, comprising:
   sliding an instrument assembly over the intramedullary device, the instrument assembly including an inner collet, a locking member, and a knob, wherein sliding the instrument assembly over the intramedullary device comprises placing the intramedullary device through an opening in the knob;
   adjusting an angle of a cutting guide associated with the instrument assembly such that the cutting guide is off-axis relative to a longitudinal axis of the intramedullary device;
   tightening the knob such that the locking member causes the inner collet to apply a clamping force to the intramedullary device, wherein tightening the knob comprises rotating the knob about the intramedullary device; and
   making a planar cut that is guided by a surface of the cutting guide.

13. The method of claim 12 wherein adjusting the angle comprises angling a translation rod.

14. The method of claim 12, wherein adjusting the angle of the cutting guide associated with the instrument assembly comprises positioning the instrument assembly such that a portion of the instrument assembly that is angled relative to the longitudinal axis orients the surface of the cutting guide to define a plane that is transverse to the longitudinal axis and non-perpendicular to the longitudinal axis.

15. The method of claim 12, wherein tightening the knob comprises tightening the knob using a threaded connection between the knob and the inner collet.

16. The method of claim 12, wherein tightening the knob causes the inner collet to apply a clamping force to the cutting guide.

17. A method for positioning an instrument relative to an intramedullary device, comprising:
   sliding an instrument assembly over the intramedullary device, the instrument assembly including an inner collet, a locking member, and a knob, wherein sliding the instrument assembly over the intramedullary device comprises sliding, over the intramedullary device, an instrument assembly in which the knob is configured to rotate relative to the inner collet;
   adjusting an angle of a cutting guide associated with the instrument assembly such that the cutting guide is off-axis relative to a longitudinal axis of the intramedullary device;
   tightening the knob such that the locking member causes the inner collet to apply a clamping force to the intramedullary device, wherein tightening the knob comprises rotating the knob relative to the inner collet; and making a planar cut that is guided by a surface of the cutting guide.

18. The method of claim 17 wherein adjusting the angle comprises angling a down rod.

19. The method of claim 17, wherein sliding the instrument assembly over the intramedullary device comprises sliding, over the intramedullary device, an instrument assembly having a locking member with an outside diameter angled relative to an inside diameter of the locking member.

20. The method of claim 17, wherein adjusting an angle of the cutting guide comprises adjusting a valgus angle of the cutting guide.

21. The method of claim 17, further comprising implanting an implant at a bone surface formed by the planar cut.

22. A method for positioning an instrument relative to an intramedullary device, comprising:

sliding an instrument assembly over the intramedullary device, the instrument assembly including an inner collet, a locking member, and a knob, wherein sliding the instrument assembly over the intramedullary device comprises sliding the instrument assembly such that the intramedullary device extends through the knob, the inner collet, and the locking member;

adjusting an angle of a cutting guide associated with the instrument assembly such that the cutting guide is off-axis relative to a longitudinal axis of the intramedullary device;

tightening the knob such that the locking member causes the inner collet to apply a clamping force to the intramedullary device; and making a planar cut that is guided by a surface of the cutting guide.

23. The method of claim 22 wherein tightening the knob causes the inner collet to apply a clamping force to the cutting guide.

24. The method of claim 22, wherein adjusting an angle of the cutting guide comprises adjusting a valgus angle of the cutting guide.

25. The method of claim 22, wherein sliding the instrument assembly over the intramedullary device comprises sliding, over the intramedullary device, an instrument assembly having a locking member with an outside diameter angled relative to an inside diameter of the locking member.

26. The method of claim 22, wherein tightening the knob comprises rotating the knob about the intramedullary device.

27. A method for positioning an instrument relative to an intramedullary device, comprising:

sliding an instrument assembly over the intramedullary device, the instrument assembly including an inner collet, a locking member, and a knob;

adjusting an angle of a cutting guide associated with the instrument assembly such that the cutting guide is off-axis relative to a longitudinal axis of the intramedullary device;

tightening the knob such that the locking member causes the inner collet to apply a clamping force to the intramedullary device, wherein tightening the knob comprises tightening the knob using a threaded connection between the knob and the inner collet; and making a planar cut that is guided by a surface of the cutting guide.

28. The method of claim 27, wherein the locking member comprises an orientation base.

29. The method of claim 27, wherein adjusting an angle of the cutting guide comprises adjusting a valgus angle of the cutting guide.

30. The method of claim 27, wherein sliding the instrument assembly over the intramedullary device comprises sliding, over the intramedullary device, an instrument assembly having a locking member with an outside diameter angled relative to an inside diameter of the locking member.

31. The method of claim 27, wherein tightening the knob causes the inner collet to apply a clamping force to the cutting guide.

32. A method for positioning an instrument relative to an intramedullary device, comprising:

sliding an instrument assembly over the intramedullary device, the instrument assembly including an inner collet, a locking member, and a knob, wherein sliding the instrument assembly over the intramedullary device comprises sliding, over the intramedullary device, an instrument assembly in which the inner collet and the knob define a common, central longitudinal axis and the locking member defines a central longitudinal axis that is angularly offset relative to the common axis;

adjusting an angle of a cutting guide associated with the instrument assembly such that the cutting guide is off-axis relative to a longitudinal axis of the intramedullary device;

tightening the knob such that the locking member causes the inner collet to apply a clamping force to the intramedullary device; and making a planar cut that is guided by a surface of the cutting guide.

33. The method of claim 32, further comprising implanting an implant at a bone surface formed by the planar cut.

34. The method of claim 33, wherein implanting an implant at the bone surface formed by the planar cut comprises implanting a tibial implant at a resected tibial surface formed by the planar cut or implanting a femoral implant at a resected femoral surface formed by the planar cut.

35. The method of claim 32, wherein adjusting an angle of the cutting guide comprises adjusting a valgus angle of the cutting guide.

36. The method of claim 32, wherein tightening the knob causes the inner collet to apply a clamping force to the cutting guide.

37. The method of claim 32, wherein tightening the knob comprises rotating the knob about the intramedullary device.

38. A method for positioning an instrument relative to an intramedullary device, comprising:

sliding an instrument assembly over the intramedullary device, the instrument assembly including an inner collet, a locking member, and a knob;

adjusting an angle of a cutting guide associated with the instrument assembly such that the cutting guide is off-axis relative to a longitudinal axis of the intramedullary device;

tightening the knob such that the locking member causes the inner collet to apply a clamping force to the intramedullary device; and making a planar cut that is guided by a surface of the cutting guide, wherein adjusting the angle of the cutting guide associated with the instrument assembly comprises adjusting a slope that the cutting guide defines for the planar cut by engaging the knob with an angled portion of the locking member.

39. The method of claim 38, wherein adjusting the slope that the cutting guide defines for the planar cut by engaging the knob with the angled portion of the locking member comprises adjusting a valgus angle of the cutting guide by engaging the knob with the angled portion of the locking member.

40. The method of claim 38, further comprising implanting an implant at a bone surface formed by the planar cut.

41. The method of claim 38, wherein sliding the instrument assembly over the intramedullary device comprises sliding, over the intramedullary device, an instrument assembly in which the locking member includes a face and the locking member defines a bore having a central axis, wherein the face is oriented transverse to the central axis and at an angle non-perpendicular to the central axis.

42. A method for positioning an instrument relative to an intramedullary device, comprising:
    sliding an instrument assembly over the intramedullary device, the instrument assembly including an inner collet, a locking member, and a knob, wherein the locking member includes a face and the locking member defines a bore having a central axis, wherein the face is oriented transverse to the central axis and at an angle non-perpendicular to the central axis;
    adjusting an angle of a cutting guide associated with the instrument assembly such that the cutting guide is off-axis relative to a longitudinal axis of the intramedullary device;
    tightening the knob such that the locking member causes the inner collet to apply a clamping force to the intramedullary device; and
    making a planar cut that is guided by a surface of the cutting guide.

43. The method of claim 42, wherein adjusting the angle of the cutting guide associated with the instrument assembly comprises positioning the instrument assembly such that a portion of the instrument assembly that is angled relative to the longitudinal axis orients the surface of the cutting guide to define a plane that is transverse to the longitudinal axis and non-perpendicular to the longitudinal axis.

44. The method of claim 42, wherein adjusting an angle of the cutting guide comprises adjusting a valgus angle of the cutting guide.

45. The method of claim 42, further comprising implanting an implant at a bone surface formed by the planar cut.

* * * * *